United States Patent
Nussbaumer et al.

(10) Patent No.: US 6,294,090 B1
(45) Date of Patent: Sep. 25, 2001

(54) ADSORPTIVE SUBSTANCE SEPARATION DEVICE

(75) Inventors: Dietmar Nussbaumer, Göttingen; Khoung To Vinh, Bockenem; Abdul Weiss; Wolfgang Demmer, both of Göttingen; Hans-Heinrich Hörl, Bovenden; Andreas Graus, Nörten-Hardenberg; Günter Pradel, Göttingen, all of (DE)

(73) Assignee: Sartorius AG (DE)

( * ) Notice: Subject to any disclaimer, the term of this patent is extended or adjusted under 35 U.S.C. 154(b) by 0 days.

(21) Appl. No.: 09/397,456

(22) Filed: Sep. 16, 1999

Related U.S. Application Data

(63) Continuation of application No. PCT/EP98/01424, filed on Mar. 12, 1998.

(30) Foreign Application Priority Data

Mar. 18, 1997 (DE) .............................. 197 11 083

(51) Int. Cl.⁷ .................................................. B01D 63/10
(52) U.S. Cl. ............... 210/321.83; 210/143; 210/321.74; 210/321.76; 210/321.85; 210/323.2; 210/489
(58) Field of Search .................... 210/143, 263, 210/323.2, 335, 341, 321.76, 321.83, 321.85, 488–490; 96/10, 52, 54; 55/520

(56) References Cited

U.S. PATENT DOCUMENTS

| 4,895,806 | 1/1990 | Le et al. . | |
|---|---|---|---|
| 4,986,909 | 1/1991 | Rai et al. | 210/198.2 |
| 5,338,450 | * 8/1994 | Maurer | 210/321.83 |
| 5,575,910 | 11/1996 | Karbachsch et al. | 210/321.75 |

FOREIGN PATENT DOCUMENTS

2001664 * 10/1993 (RU) .............................. 210/321.85

* cited by examiner

*Primary Examiner*—Joseph W. Drodge
(74) *Attorney, Agent, or Firm*—Chernoff, Vilhauer, McClung & Stenzel, LLP

(57) ABSTRACT

An adsorptive separation device is disclosed having at least one spiral wound adsorption membrane situated around the periphery of a core mandrel wherein the flow is radial from a feed plenum situated between the core mandrel and the membrane, through the membrane to a permeate plenum located between the membrane and a housing for both the core mandrel and the spiral wound membrane. An array of such separation devices is also disclosed showing connections in parallel, in series, in both parallel and in series and in tandem.

32 Claims, 17 Drawing Sheets

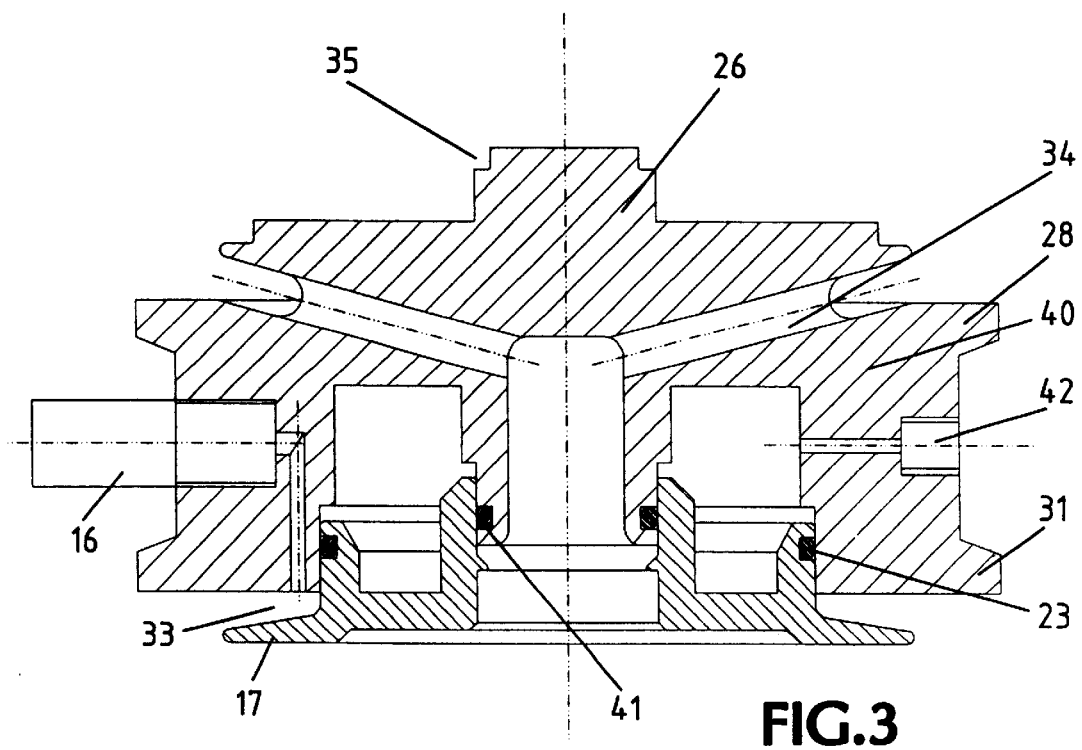

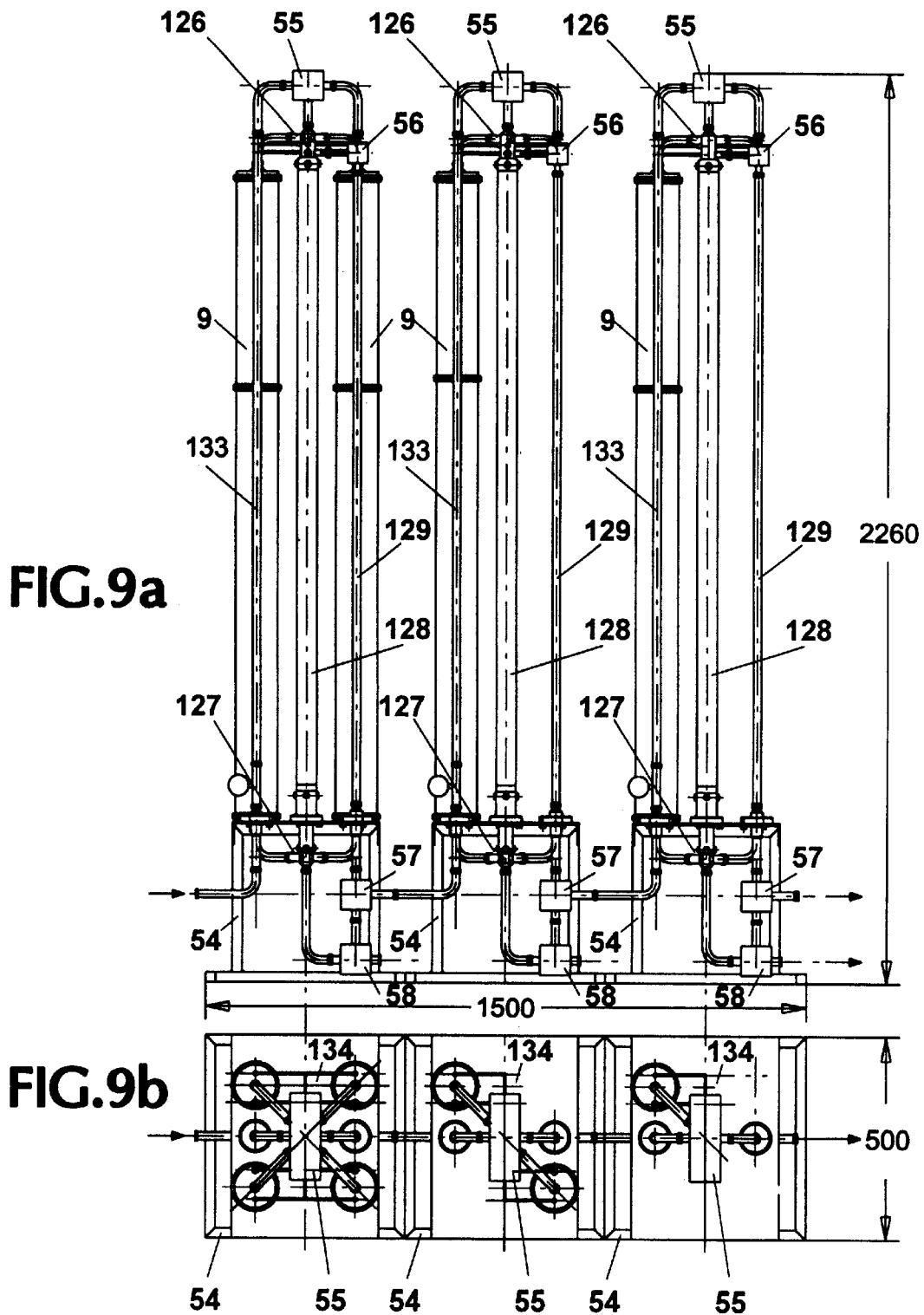

ADSORPTIVE SUBSTANCE SEPARATION DEVICE

This is a continuation of PCT/EP 98/01424 filed Mar. 12, 1998, the priority of which is claimed pursuant to 35 USC 120. The priority of DE 197 11 083.5 filed Mar. 18, 1997 is also claimed pursuant to 35 USC 365.

BACKGROUND OF THE INVENTION

The invention concerns apparatus for separation of substances by permeation of liquids through porous adsorption membranes.

Adsorptive separation in the context of the present invention means separation or purification of specific substances from a liquid phase medium, which are specifically adsorbed by a solid adsorbent. The medium containing the substances to be separated and/or purified is fed to or through the solid adsorbent whereby adsorption takes place, then separated by means of one or more elution liquids (eluants) that are forced through the adsorbent under pressure. Depending on the degree of interaction between the substances in the medium with the solid adsorbent and with the eluants, the substances are retained with different strength by the adsorbent, resulting in fractionation of the substances from the adsorbent. The substances to be separated from the medium can either be adsorbed alone or together on the adsorbent. In the latter case, the medium is filtered with the target mixture to be separated through the adsorber module, until the target-depleted substance appears at the outlet of the module. It can be eluted separately from other substances retained on the adsorbent with appropriate eluants that are flowed through the module, referred to as stage elution. Undesired substances or contaminants may also be separated from the medium.

Another area of application of adsorbtive separation by the present invention is chromatography, wherein only part of the adsorption capacity of the adsorber is utilized for adsorption and separation of the adsorbed components is conducted using different volumes of eluant for elution.

The interactions between solid and liquid phases, therefore, play an important role in adsorptive separation, wherein the solid phase must exhibit a high specific affinity surface to achieve high efficiency, and therefore must have either limited particle size or high porosity. Since limits are imposed on the use of extremely fine solids, in practice highly porous matrices are generally used as solid phases. The use of porous matrices means that the kinetics of the fundamental process of adsorption/desorption, i.e., the interaction between the components of the liquid phase with the solid phase, is superimposed on the kinetics of mass transport into and out of the porous matrix. Since mass transport in known matrices (as in particulate matrices) primarily occurs by diffusion, and since diffusion coefficients of liquids tend to be low, there is an inherent limitation on the efficiency of this type of adsorptive separation.

On the other hand, nonparticulate matrices having continuous pore structures such as porous membranes offer the possibility of primarily convective mass transport under a pressure differential, thus eliminating the aforementioned diffusion limitation on efficiency.

In the context of the present invention, the term "adsorption membrane" broadly means membranes that carry functional groups, ligands or reactants on their internal and/or external surfaces that are capable of interaction with at least one substance of a liquid phase in contact with them. Exemplary types of adsorption membranes include cationic, anionic, ligand, affinity or other activated membranes that in turn may be classified according to their particular functional groups, ligands or reactants.

The term "porous adsorption membrane" refers to membranes whose average pore diameter preferably lies in the microfiltration range, e.g., between about 0.1 $\mu$m and about 15 $\mu$m. The thickness of porous adsorption membranes preferably lies between about 100 $\mu$m and about 500 $\mu$m.

Methods and apparatus for adsorptive separations by permeation of liquids through porous adsorption membranes are known. See, for example, U.S. Pat. No. 5,575,910, wherein a combination of pressurized axial and radial feeds are used. To increase adsorption capacity, a plurality of membrane adsorption packs, each formed from a number of planar sheet of porous adsorption membranes, are used in a stacked arrangement with spacers between each pack. Although efficient separation is achievable with such a device, it has a drawback in that fabrication results in significant waste of valuable adsorption membrane material. Moreover, an increase in the number of planar sheets of porous adsorption membranes is associated with a reduction in flow performance and relatively rapid blinding of the upper layers of the adsorption membranes packs.

Use of spiral wound adsorption material is known from U.S. Pat. Nos. 4,895,806 and 4,986,909, this form tending to minimize waste of valuable adsorption membranes. Both patents disclose a sheet of adsorption membrane wound onto a perforated central tube which filters by forcing the liquid medium from the outside radially inwardly by application of a pressure differential. A shortcoming of such designs is that the permeation-effective surface in a winding tends to diminish from the outside in. Furthermore, if the diameter of the perforated central tube is small, the flux of the device is correspondingly small; on the other hand, if the tube diameter is large, the dead volume of the device is also large. Such spiral wound designs have the further drawbacks that the flow performance diminishes rapidly and filter lifetime is relatively limited, owing to membrane fouling and defects. Yet another drawback of such spiral wound designs is that they possess a rigid configuration that does not permit flexible adaptation to a variety of separation tasks.

The aim of the present invention is therefore to devise an apparatus, configured with an adsorber module, to conduct adsorptive separations by permeation of liquids through porous adsorption membranes, the apparatus being characterized by minimal dead volume, optimal active adsorption filtration volume with high binding capacity, high flux and long lifetime, as well as by a high degree of flexibility for adaptation to a wide variety of separation tasks. A related goal of the present invention is to propose applications for the use of inventive device for adsorptive substance separations.

These goals and others which will become apparent to those skilled in the art are achieved by a uniquely designed device having the function and adaptability summarized and described in detail below.

BRIEF SUMMARY OF THE INVENTION

According to the present invention there is provided a separation device for separations by permeation of liquids through a porous adsorption membrane, comprising a cylindrical housing with liquid input and liquid output; a housing accommodating at least one cylindrical adsorber module comprising a core and spiral wound porous adsorption membrane, the module being arranged substantially concentrically in the housing; the module further being provided with an annular feed plenum on its inner side and forming with the outer wall of the housing an annular permeate plenum on its outer side; the feed plenum, the permeate plenum and the liquid input and output being arranged so that liquid feed flows from the liquid input to the feed plenum and permeates through the adsorptive membrane to the permeate plenum and then is discharged through the liquid output. Liquid feed is preferably channeled through radial holes in the core to the annular feed plenum, while liquid permeate is directed through radial channels in the bottom of the device to the annular permeate plenum. Thus, the overall flow pattern of the liquid medium to be treated is radially from inside to outside of the spiral wound adsorption membrane.

This permeation of the adsorber module from the inside out results in high flow performance and lifetime, in a substantial reduction of membrane fouling, and in the protection of the adsorption membranes from mechanical defects during permeation operation.

The device can be used for selective separation and purification of materials such as biospecific molecules, proteins, enzymes, ionogenic substances, and metal ions (especially heavy metal ions) from different media. The device may be used in laboratory, pilot plant and production work. It is designed so that scale adjustment (both scale-up and scale-down) work is possible. Other applications include the fields of biotechnology, genetic engineering, pharmacy, chemistry, the food and beverage industry, and environmental protection.

BRIEF DESCRIPTION OF THE SEVERAL VIEWS OF THE DRAWINGS

FIG. 3 is a vertical section through a connection piece for series connection of two adsorber modules in an exemplary embodiment I-type device of the invention.

FIGS. 9a–9b are vertical and plan sections of a three-stage adsorptive separation installation, consisting of 12 modules in four housings in the first stage, 6 modules in 2 housings in the second stage, and 3 modules in a single housing in the third stage, drawn to scale with dimensions in millimeters.

DETAILED DESCRIPTION OF PREFERRED EMBODIMENTS

Figure 1:
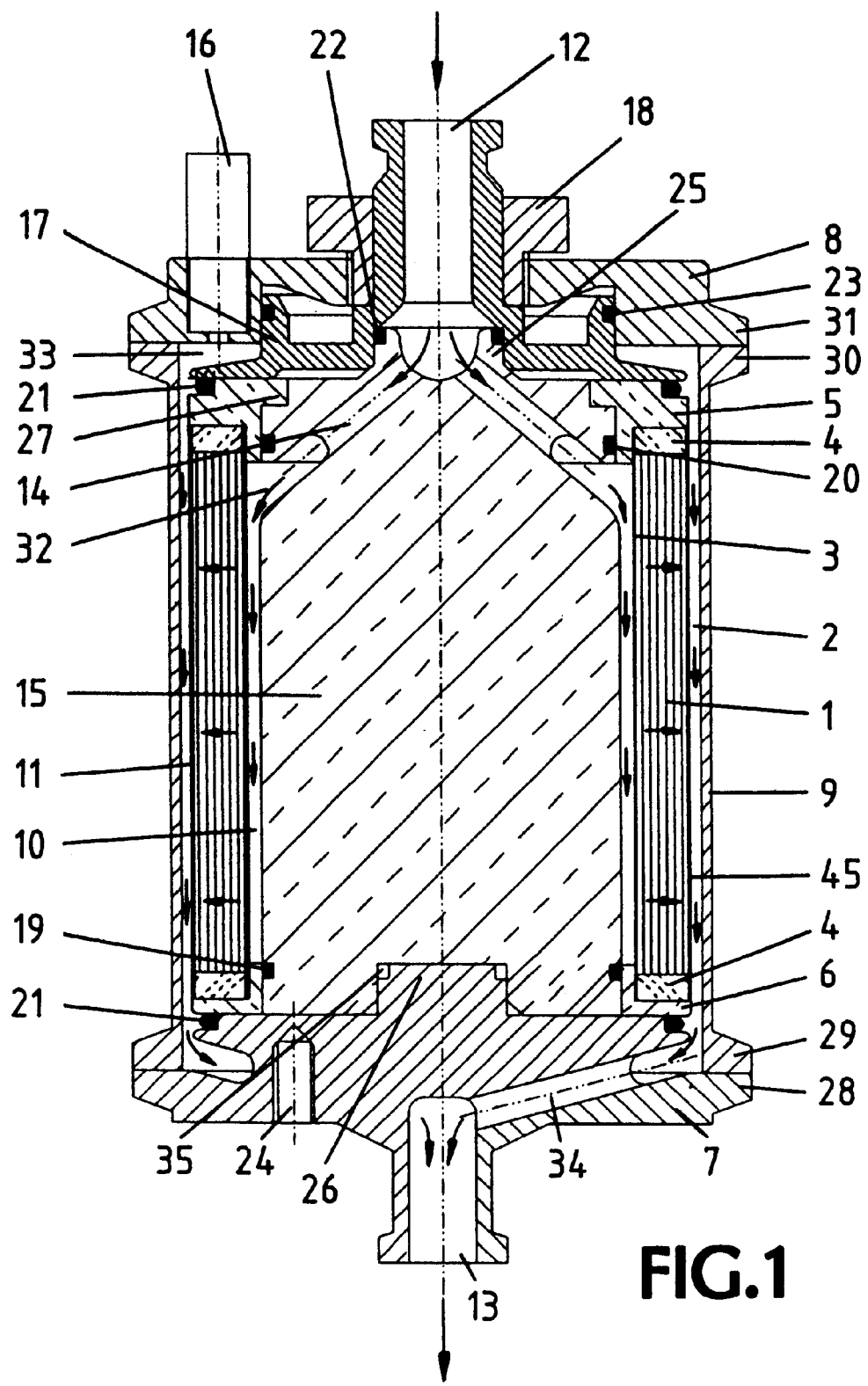
FIG. 1 is a vertical section through an exemplary device of the invention denominated as embodiment I.

The inner windings of membrane material of a conventional spiral wound adsorption membrane wherein the flow is from the outside to the inside obviously serve as a filter support for the outer windings with the result that the inner windings are compressed during filtration. Because of their high pore volume, such spiral wound adsorption membranes are reduced in thickness during compression, causing a reduction in their flow throughput or flux. In the case of a spiral wound membrane exposed to pressure from the outside, however, this reduction in thickness has another more serious consequence than flux reduction. Because the inner windings are further compressed by exposure to pressure, the diameter of the inner layers diminish, as does the diameter of the individual windings, the degree of diminishment increasing with increasing numbers of windings. This diminishment also causes distortion of the cylindrical shape of the spiral wound membrane, which in turn causes corrugation and crease formation, leading to nonuniform flux and nonuniform loading, which in turn lead to premature local breakthrough of the target substance. The practical result of this is that the dynamic binding capacity of the adsorption membrane is very much lower than would be expected for a given surface area of adsorption membrane. These effects are further intensified by the fact that the adsorption membrane is subject to severe mechanical stress at the creases, often resulting in membrane breaks.

The superiority of the devices of the present invention having cylindrical adsorber modules traversed from the inside to the outside of the wound adsorption membrane material relative to those that are traversed from the outside in becomes most apparent after longer operation. Naturally, the windings of the adsorption membranes traversed first are particularly susceptible to clogging by particulate contaminants of the medium being filtered and by fouling effects. In conventional spiral wound adsorption membrane separation devices, as soon as the outermost layer is clogged, the effective operating pressure of the device drops throughout every layer of the wound membrane due to the compression transmitted to the inner layers.

Such drawbacks are avoided by flow from the inside out. If, in the extreme case, the innermost layer is clogged, it is exposed to a tensile stress with the result that the membrane sheet material is stretched and not compressed, which prevents creasing. The behavior of spiral wound adsorption membrane during pressurization is comparable to that of a tube, which tends to collapse when pressure is applied to the outside, whereas no significant dimensional changes occur upon pressurization from the inside. The use of an annular feed gap instead of a perforated central tube on the inside of a cylindrical adsorber module and an annular permeate gap on the outside means that dead volume can be minimized.

The feed and permeate annular gaps or plenums, in a preferred embodiment, are held open by spacers, which also function as supports for the adsorber module. All materials familiar to one skilled in the art for construction of permeation modules can be used as spacers. In an especially preferred embodiment of the invention, the spacers are formed by grooves that are situated on the surface of the cylindrical core and on the inside surface of the outer wall of the housing. The grooves may have different geometries varying from straight to continuously helical, for example.

It was surprisingly found that there exists a relationship between the dimensioning of the annular feed and permeate plenums of the device and the flow performance of the adsorption membranes, which permits dimensioning of the annular plenums such that optimization of the adsorption capacity of the adsorber device is virtually guaranteed.

The flow cross sections of the annular plenums are controlling for the hydraulic pressure drop, for both the feed and the withdrawn permeate. This pressure drop should be as small as possible, not only because pressure losses in the annular plenums compromise the flux attainable with the device at a given operating pressure, but because they lead to local variations in pressure differential over the length of the device. Local variations in pressure differential cause local variations in flux, with the result that the binding capacity of the adsorption membrane is exhausted in different locations at different times. Since the total useful binding capacity of an adsorber is exhausted as soon as the first breakthrough of a target substance appears at one site, a high pressure drop in the internal and/or external annular plenum results in a reduction of useful binding capacity.

If one attempts to avoid the adverse consequences of large pressure drops across the annular plenums by the provision of particularly wide annular channels (the width of an annular channel being understood to mean the difference between its external and internal radius) there exists the possibility of over dimensioning; oversized gap widths not only cause an excessive dead volume, but also a needlessly large apparatus volume. High dead volume of an adsorber unit adversely effects its performance. A large apparatus volume, among other things, results in high manufacturing costs.

The optimum annular gap width is chosen so that the adverse phenomena caused by both under- and over-sizing are avoided. The optimal gap width is dependent on the specific flow performance of the adsorption membrane, the thickness of the adsorption membrane, the ratio of inside to outside diameter of the hollow cylinder formed by the spiral wound adsorption membrane and the length of the adsorber module. The dependence of optimal gap width on the length of the adsorber module hampers its empirical determination, insofar as it rules out direct transfer of results obtained on small test models to large units. For all practical purposes, this means that for empirical optimization of the gap widths, actual size experimental models must be produced using the prescribed adsorption membrane and the actual flow and breakthrough behavior must be investigated while varying gap widths.

According to the invention, it is now possible to determine optimal gap widths much more economically and yet accurately by the use of a dimensionless parameter developed as a result of careful study of the operation of devices of the present invention. The dimensionless parameter is termed the "resistance parameter" (symbolized by the letter A), and permits mathematical relationships to be established between the geometric and hydraulic specifications of devices of the invention on the one hand and the quality-determining properties of the devices on the other hand. The resistance parameter A is defined as follows in the case of an inside-to-outside radially traversed membrane winding:

$$A = L \sqrt{\frac{8 \cdot D \cdot d}{[(R_2+k)^2 - R_2^2] \cdot \left[(R_2+k)^2 + R_2^2 - \frac{(R_2+k)^2 - R_2^2}{\ln\left(\frac{R_2+k}{R_2}\right)}\right] \cdot \ln\left(\frac{R_2}{R_1}\right)}}$$

wherein:

$R_1$=inside radius of the spiral wound adsorption module in cm;

$R_2$=outside radius of the spiral wound adsorption module in cm;

k=width of the outer annular permeate plenum in cm;

L=length of the spiral wound adsorption module in cm (when several adsorber modules are connected in tandem in a housing, L is the total length of the module);

D=adsorber membrane flux, measured as $cm^3 \cdot cP/cm^2 \cdot min \cdot bar$; and p1 d=thickness of the adsorber membrane used in cm.

The definition of A is derived using simplifying assumptions from the flow conditions in an apparatus according to the invention, those assumptions being validity of the Hagen-Poiseuille Law in the annular gaps, and a linear relationship between pressure differential and flow rate through the membranes, ignoring the hydraulic head. The local static pressure in the annular gaps and, from them, the local static pressure differential, can be approximated ignoring the different flow resistances in the internal and external annular gaps. The following criteria are essential for evaluation of the performance of an adsorber membrane separation device:

the average pressure differential $\Delta P_m$, which determines the attainable filtration performance;

the maximum pressure differential, which determines the beginning of breakthrough of the target substance and in turn the loss-free utilization capacity of the adsorber, symbolized by $K_n$.

The following mathematical relations have been found to exist, wherein $P_0$ is the pressure difference between the input and output of the adsorber and K is the binding capacity of the adsorber without flow resistances in the annular gaps:

$\Delta P_m = P_0 [\sin A/A(\cos A + A \sin A)]$ $K_n = K(\tan A/A)$

Using the stated values for parameters actually used in the Examples, exemplary calculations are set forth below (the example with only one winding illustrates the adverse effect of annular gaps dimensioned too narrowly).

L=100 cm; $R_2$=48 mm; k=2 mm;

D=150 $cm^3 \cdot cP/cm^2 \cdot min \cdot bar$; d=300 $\mu m$

| Number of Windings | $R_1$ | A | $\Delta P_m/P_0$ | $K_n K$ |
|---|---|---|---|---|
| 1 | 47.7 | 0.425 | 0.806 | 0.944 |
| 14 | 43.8 | 0.112 | 0.984 | 0.996 |

-continued

| Number of Windings | $R_1$ | A | $\Delta P_m/P_0$ | $K_n K$ |
|---|---|---|---|---|
| 29 | 39.2 | 0.058 | 0.996 | 0.999 |
| 67 | 27.9 | 0.024 | 0.999 | 1 |

The gap widths of the annular gaps are preferably chosen so that the outer and inner annular gaps have the same volume. The outer annular gap therefore has a smaller gap width and therefore a higher flow resistance than the inner annular gap and is used to evaluate the pressure drop.

Although disposable devices wherein the adsorption membrane is rigidly connected to the housing can be produced according to the present invention, the preferred embodiments utilize multiple units in various combinations to accommodate a large variety of scale, which permits refitting a separation device or an array of such devices with a minimum of material. This is achievable by virtue of the fact that the device is constructed from the five basic components comprising the housing, the top and bottom elements, the adsorber module and the core mandrel. Auxiliary components that are described in detail further below are added to this. Thus, interchangeable components can be used on a process scale for adsorber modules containing different numbers of windings in the adsorption membrane layer. In other words, although adsorber modules having different numbers of windings do have different core diameters, they can be used in the same housings. This may be achieved according to the invention by making the dimensions of the connection piece between the cover element and the core the same for all modules, regardless of the number of windings.

As with any new technology, problems of scale-up and scale-down must be managed. A preferred variant of the present invention, namely, embodiment I, offers the possibility of gap-free scale-up and scale-down over a wide range. It is essential that the experimental results obtained with small scale units are directly transferable to scaled-up systems. In this case, a so-called unit module is used as point of departure, the length of which expediently corresponds to the manufacturing width of the adsorption membrane. The scale-up principle is then the parallel connection of unit modules, both within a common housing and in several housings, and the scale-down principle is the shortening of unit modules.

Another advantage of embodiment I-type design of the invention lies in the fact that the housing can be readily produced from metals and machinable plastics, and components produced from different materials are freely combinable with each other. In fact, it would be technically possible to use the same material during scale-down as during scale-up. Whereas a robust design material, such as stainless steel, is to be preferred in an industrial installation, cost-effective, lightweight units made of polymers can be advantageously used during preliminary experiments on a laboratory scale.

There is often a requirement in experimental devices to use transparent materials, such as glass or Plexiglas. Even when neither the target substance nor contaminants being bound have an intrinsic color, visual evaluation of the chromatographic trend can permit definitive conclusions by observation of the schlieren produced by different refractive indices. Locally different refractive indices are based on different concentrations of dissolved substances, be it the target substance, a contaminant or a buffer or eluant additive. This requirement may be met, in principle, with the design of embodiment I, but only with intolerably high requirements for material processing of the glass or Plexiglas.

However, such a requirement is readily met with embodiment II. Embodiments I and II differ primarily in that the mechanical connection between the top and bottom elements and the take-up of the axial sealing forces occurs through the housing in embodiment I, whereas they occur through the core in embodiment II, where the task of the housing is reduced to collection of the permeate. As a result, in embodiment II glass and/or Plexiglass may be used for the housing. The adsorber module is identical for both embodiments.

Separation devices of the designs of embodiments I and II correspond, in terms of flow, to what is known in the art as "dead end filtration," whereby the entire medium being treated flows through the adsorbent and is removed from the apparatus as permeate. However, it is also possible according to the invention to accomplish so-called "cross flow" filtration, where only part of the supplied medium flows through the adsorbent and is removed as permeate, while another part is removed again at the end of the inner annular feed plenum as retentate, which is advantageous when the medium contains particulate contaminants, which cannot be arbitrarily concentrated and would otherwise blind the adsorbent membrane material. The permeate and retentate can either be removed separately or remixed prior to removal. In the latter case, the additional advantage is that the high particulate concentration, which, in the extreme case, can lead to a pasty consistency and to resulting separation difficulties, is maintained no longer than absolutely necessary.

Embodiment III represents an apparatus of the type wherein remixing of the permeate with the particle concentrate occurs within the device, the ratio of permeate to retentate being regulated by a needle valve-like design. In this embodiment a particle suspension containing the target substance is supplied as feed, which is depleted in the target substance, then removed. The target substance can be recirculated to attain complete adsorption.

Removal of a target substance from a liquid feed medium and its recovery in the form of an eluate with the highest possible concentration are featured in embodiments I-III, for which minimization of dead volume is important.

However, the invention also has application in separation tasks wherein the concentration of eluate is of little or no significance such as in the removal of contaminants like pyrogens, DNA fragments or interfering enzymes such as proteases. For this purpose a device of the design of embodiment IV is preferred, wherein supply of the feed occurs from below. Flow in the annular plenums is the same as in the other preferred embodiments. Removal of permeate occurs via a separate connection in the bottom cover. The sealing sites are dimensioned so that the same modules as for the other embodiments can be used. According to a proposed application of embodiment IV, an option is to provide low capacity adsorber modules having a small number of windings for the removal of contaminants generally present only in low concentration, together with a so-called "guard filter" that functions as a safety measure to eliminate contaminants not normally present. Comparatively high flow rates are thus attainable, which means that the simplifying assumptions made in the above-described mathematical model for determining annular gap widths (laminar flow and ignoring dynamic pressure) are no longer valid. The annular gaps are therefore overdimensioned relative to the calculated values for safety, especially since dead volumes are of secondary significance here.

Another feature of the present invention permits avoidance of the adverse effects of dynamic pressure by the provision of a special flow configuration in the diversion of the feed from the core mandrel into the inner annular feed plenum, whereby abrupt changes in direction of the fluid feed are avoided and entry into the annular feed plenum occurs at the flattest possible angle.

In general, it may be said that the higher the concentration of target substances in the feed, the higher the required number of windings of the membrane material will be. On the other hand, the smaller the number of windings is, the smaller the cylinder diameter will be, so as to minimize the dead volume of the separation device. A lower limit of 5 windings and an upper limit of 150 is preferred for manufacturing. A preferred upper limit of the outer cylinder diameter is 200 mm, while the lower limit in, for instance, laboratory scale units, is 5 mm. The preferred ratio of inside to outside cylinder diameter may vary over broad limits, namely, between 0.25 and 0.95.

The invention permits coverage of a broad spectrum of applications at a minimum cost for a given application with a modular component system wherein individual components are largely interchangeable, and wherein a series of adsorber modules, the windings of which are graded, for instance, in a ratio of about 1:2. For example, adsorber modules according to the invention with 8, 15, 30 and 60 windings can be produced for use in housings having an inside diameter of 100 mm.

The hollow cylindrical adsorber module of the present invention, in addition to the layer with at least one winding of an adsorption membrane, consists of lower and upper end caps, a potting compound to embed the adsorption membrane in the end caps, and in a preferred embodiment, inner and outer support elements. The end caps, preferably formed of a thermoplastic material, are attached on the open ends of the hollow cylindrical adsorber module and extend across it. They embed the peripheries of the adsorber module in fluid-tight fashion wherein at least one of the end caps has an annular design, preferably both having an annular design.

The outer support elements are fluid-permeable and function not only to support the membrane against hydraulic pressure fluctuations and internal pressure variations, but also to lend to the adsorber module the required rigidity for handling, for example, during insertion into the housing. In the simplest cases, cylinders produced by the sealing of fabrics can be used as the outer support element. The outer support element need not be designed to withstand the full hydraulic pressure differential between inner and outer plenums because this pressure differential is largely taken up by the individual windings of the membrane.

The inner support element has virtually no exposure to pressure under operating conditions and could therefore in principle be omitted. However, in practical operation it is useful to periodically back flush at low pressure to prevent any blinding of the innermost winding, during which the inner support element prevents collapse of the membrane winding.

The support elements are preferably somewhat longer on both ends than the width of the adsorption membrane sheet from which the winding is produced, preferably approximately 2 to 10 mm, so that they are well-anchored in the potting compound. Suitable materials for forming the support elements include polymers such as polypropylene, polyesters, polyamides, and polyurethanes and metals such as corrosion-resistant special steels, especially those with high chloride resistance.

If a metallic support element is used, a nonmetallic spacer such as a polymeric fabric is preferably inserted between the adsorption membrane and the support element in order to avoid direct contact between the membrane and metal. This spacer may comprise several layers, which has the advantage of increasing the wall thickness of the hollow cylinder, particularly desirable when the module comprises a small number of windings. When the number of windings is below 15, additional layers of spacer material may be used to take up the slack, thereby enabling the use of the same end caps as for 15 windings. Materials suitable for the spacers include fabrics, nonwoven web materials, perforated sheets, and perforated films, which may be bonded to the cylinders thermally or with an adhesive, and molded polymeric articles. In the case of steel fabrics, wire thicknesses between 0.2 and 0.5 mm at mesh widths between 0.3 and 1 mm are preferred. In polymeric fabrics wire thicknesses between 0.5 and 1 mm with mesh widths between 1 and 2 mm are preferred. For nonwoven materials such as polypropylene the preferred thickness range is between 0.2 and 1 mm.

The function of the potting compound is to seal the ends of the adsorption membrane winding and join the support elements, adsorption membranes, and end caps together. It is essential for reliable sealing that the potting compound contact, in liquid form under pressure, the front surfaces of the adsorption membrane winding. Effective potting occurs using a winding device and a casting device. The winding device consists of the winding core and two shoulders A and B. The outside diameter of shoulder A corresponds to the inside diameter of the outer support element, whereas shoulder B is only turned to this diameter on the length of the protruding part of the outer support element, so that a stop still exists. The inner support element is mounted on the winding core, then on the shoulders. These are hollowed out to accept the protruding part of the support element. The outer part of the shoulders limits the position that the edges of the adsorption membrane winding are to assume. After tight winding of the adsorption membrane, the end of the sheet is generally glued to the winding, for example, by spot or linear application of the liquid potting compound. The outer support element is then pushed over shoulder A onto shoulder B, up to the stop. Casting of the winding can occur either in a working process with application of the end caps, or by means of a removable mold in which the end caps are subsequently attached. The first method is preferred, but requires a more demanding design of the winding and casting device.

Both thermosetting resins such as polyurethane, epoxy and especially silicone rubber and thermoplastic resins such as polypropylene are useful as potting compounds. It is essential for the casting process that the liquid potting compound be introduced from below to the upright winding and that, as soon as it makes contact with the edge of the winding, recognizable by emergence over the edge, its introduction is interrupted or continued so slowly that no noticeable excess of the potting compound occurs. In this manner the potting compound not only fills the space up to the adsorption membrane winding bubble-free, but also enters between the membrane edges and the membrane pores, resulting in reliable sealing of the edges. The potting process may be accelerated by use of centrifugal casting as familiar to one skilled in the art for casting of hollow fiber and capillary modules.

As explained, the end caps produce the sealing connection between the adsorption membrane winding and core. Sealing of the inner annular feed plenum is explained in conjunction with the design of the core mandrel. The upper end cap preferably has a cross piece on its inside that fits a corresponding recess in the core mandrel. This cross piece, on the one hand, serves for exact positioning of the module on the stop and also transfers the weight of the module to the core mandrel. This is of particular significance if several adsorber modules are stacked in a single housing. Without such a cross piece connector element, the weight of all the other adsorber modules would impinge upon the lowermost module, which would lead to compression of the inner and outer support elements. The upper end cap also has a groove on the outside to accept a sealing element such as an O-ring. The function of this seal is not separation of the feed and permeate, since this occurs between the inner surfaces of the end caps and the core. Instead, sealing at this site prevents the permeate, eluate or cleaning agent from penetrating into the gap between the end cap and cover element (or between the two end caps in several modules), which would otherwise lead to contamination.

The end caps may also be formed from potting compound simultaneously and in connection with potting of the membrane. If an elastic, self-sealing material such as silicone rubber is used for this purpose, the sealing elements between the module and core may be omitted. If end caps are mounted as separate components, they are preferably provided with undercuts that allow additional mechanical anchoring of the potting compound in the end cap. This is the case with potting compounds, such as silicone resins that are preferred for pharmaceutical applications, that have no adhesion to the cap material.

In a preferred embodiment, adsorption membranes with different adsorption properties are accommodated in the same adsorber module. This is useful in applications when several target substances or contaminants are to be bound simultaneously. To this end, two or more adsorption membranes may be wound, one over the other, or two or more different membranes may be wound in parallel, allowing them to be traversed in alternation.

In still another variation of the invention, adsorption membranes with the same adsorption properties but different porosities may be combined in one adsorber module so that the more favorable breakthrough characteristics of fine-pore adsorption membranes are used while the drawback of their lower flux is minimized. In such a case, a more coarse-pore adsorption membrane is arranged on the feed side, while a finer-pore adsorption membrane is nearer the permeate side. Another reason for the use of different membrane porosities is to allow the flux of the adsorber module to be standardized. Uniformity of flux is of particular significance during parallel connection of several adsorption modules, which is a characteristic peculiar to adsorption modules as compared to ordinary filtration modules. Whereas during parallel connection of sterile filtration units particularly high flux of a single unit can have only a positive effect on the performance of the entire system, if each of the parallel-connected units actually carries out sterile filtration the conditions during adsorption are quite different. If one of several parallel-connected adsorber modules has higher flux with the same adsorption and binding capacity, it is exhausted before the others, which leads to breakthrough of the target substance without exhaustion of the adsorption capacity of the other modules. For these reasons, when the available adsorption membrane cannot be produced with exactly the same flux, it is expedient to set precisely specified fluxes of the adsorber module by a combination of membrane charges of higher and lower fluxes in the individual modules.

As previously mentioned, a guard or protective filter may be arranged on the inside of the hollow cylinder of the adsorber module. The guard filter is preferably configured as a replaceable, cylindrically shaped filter. A fine-pore microfiltration membrane is suitable for this purpose, but is preferably fabricated from the same adsorption membrane from which the adsorber module is constructed so as to have the same adsorption properties as the adsorption membrane material employed in the module, because coagulation or corrosion by products can be of the type that cannot be retained by inert filter material. In operating conditions, under which irreversible blinding of the adsorption membrane can occur, the membrane layer traversed first is generally involved almost exclusively. For this reason, it is generally preferred to include a single layer of adsorption membrane that is easy to replace. The protective filter, consisting of the adsorber filter material, is preferably designed as a membrane tube, produced by sealing or gluing together the ends of a sheet of adsorption membrane. Its diameter is adjusted to the inside diameter of the inner support element and it is inserted loosely in the hollow cylinder, so that it is pressed against the inner support by the operating pressure. Special sealing on the ends is then not absolutely essential. The advantage of the protective filter is that the expense connected with its replacement is so limited that it is in no relation to the damage that would otherwise occur by an adsorber module rendered unusable.

The outside diameter of the core mandrel, together with the inside diameter of the adsorber module, determines the height of the inner annular feed plenum. The core mandrel helps position the adsorber module or modules in the housing, displaces volume to reduce the dead volume, and distributes the feed. In embodiment II the core mandrel has the additional function of mechanically joining the bottom and cover elements and taking up the axial sealing forces.

In embodiment I there is the additional function, if other parallel-connected adsorber modules are situated downstream of it, of conveying the feed to downstream modules. Two different designs of the core mandrel must therefore be distinguished in embodiment I, depending upon whether additional adsorber modules are situated downstream of the first. In a first design, the core mandrel has channels, e.g., in the form of holes, on both ends as an extension core for passage of the feed, or in a second case, only on the upper end. This means that for refitting an embodiment I-type device with a different type of adsorber module, it is sufficient to replace the adsorber modules and the cores, while the housing top and bottom elements can be retained.

The core mandrel may be fabricated from a solid material and from hollow elements impermeable to fluids. The same materials from which the end caps may be produced are also suitable, namely, polyacetals, polypropylene and polyamides, with polyacetals being preferred.

The inside diameter of the housing, together with the outside diameter of the adsorber module, determines the height of the outer annular feed plenum. The general function of the housing is the collection of permeate. In embodiment I the housing has the additional functions of mechanical joining of the top and bottom elements and take-up of axial sealing forces. In embodiment I, housings with clamp connections and an O-ring seal or having flange connections with the bottom element are preferably used. Mechanical contact between the housing and the top or bottom element is essential in the connection, in order to guarantee geometrically defined conditions. Clamp connections with flat seals, in which nonuniform compression of the seal can occur, are not suitable. The module system of Variant I makes it possible, in a simple fashion, to equip existing housings for a larger number of modules by employing extension pieces.

Through the bottom element a largely rotationally symmetric takeoff of permeate to an axially arranged permeate outlet is produced via approximately 3–8 holes, this connection preferably being designed as a molded-on clamp connection. The cover element also preferably has an axial clamp connection and, in preferred embodiments, a vent through the outer annular permeate plenum. Ventilation of the outer annular permeate plenum must be ensured, because air therein would lead to a higher hydrostatic pressure differential between the inner and outer annular plenums in their lower regions, with the result of premature breakthrough of the target substance in these regions.

Although any fitting such as a simple bleed-off screw may be used for the vent, the use of a screwable return valve, with or without spring loading, is preferred, wherein the sealing element is arranged directly in a corresponding hole of the top or cover element. A blocking device is mounted in the branch of the return valve. When this is opened, the outer annular permeate plenum is ventilated by the pressurization prevailing in the separation device. The advantage of the return valve, on the one hand, consists of the fact that sealing occurs directly in the top element, and a dead space that can lead to contamination is avoided. On the other hand, it is also possible to ventilate several parallel-connected modules, wherein the branches of the return valves are connected to each other, via a common valve. This is of particular significance for automatically operating units, wherein venting is controlled via a process controller.

It is expedient, especially after cleaning of the adsorber module with aggressive media, to carry out rinsing or flushing in the bypass with a rinsing buffer via the ventilation opening, which may also be automated with a process controller. In this connection, another function of the vent is to flush the upper region of the outer annular permeate plenum. In order to distribute the liquid stream as evenly as possible over the entire outer annular permeate plenum, a continuous groove is provided in the top element. The flushability of the upper part of the outer annular plenum is significant, because under operating conditions the liquid in this region exhibits no compulsory flow.

It was unexpectedly found that when a spiral wound adsorber module is traversed radially from the inside out with the feed under the influence of a pressure differential higher flow performance and higher resistance to the operating pressure are achieved than during flow through the same separation device from the outside in. Accordingly, the apparatus of the invention is preferably constructed and operated with a vertical cylinder axis. Another surprising discovery was that when feed is supplied from above, the eluate, which has high density owing to a high concentration of desorbed target substance as well as a high content of electrolytes in the eluant, can flow out downwardly more easily. Supply of the feed and discharge of the permeate preferably occur on opposite ends of the apparatus.

To start up the separation device it is first filled from below with liquid and the outer annular permeate plenum is vented via a vent of the type described. However, it is also possible to configure the separation device so that supply of the feed into the inner annular feed plenum occurs from below; in this case, the vent in the top element is connected to the inner feed plenum.

The invention also permits the construction of installations for adsorptive material separation which are characterized by great flexibility. For example, based on embodiment I alone there are two possibilities for parallel connection of adsorber modules or devices: (1) by parallel connection of several individual modules in a single housing; and (2) by parallel connection of several identically equipped housings. In the second case symmetric feed inlets and permeate outlets must be considered, wherein crosspieces are utilized in the feed and permeate conduits. Whereas parallel connection of the adsorber modules can in principle only worsen breakthrough of the target substance because nonuniformities in flux or binding capacity mean that breakthrough does not occur simultaneously in all modules, series connection, in principle, leads to an improvement of the target substance breakthrough trend.

Larger installations are preferably built by a combination of both parallel and series connections. Use of a preferred system of modules with stepped gradations of the module windings in a 1:2 ratio results in particularly advantageous possibilities. If, for example, n adsorber modules with 60 windings of the adsorption membranes are connected in parallel in the first stage, n/2 modules with 30 windings are connected in the second stage, and n/4 modules with 15 windings are connected in a third stage, the pressure drop in all three stages is roughly the same and the binding capacity of each subsequent stage is 1/4 that of the preceding stage. Because the target substance that penetrated during creeping breakthrough is trapped by the following stage, the overall binding capacity (which can be utilized up to a specific concentration of target substance in the permeate), can be significantly increased.

The particular advantage of the mentioned stepped gradation lies in the fact that the pressure drop is uniformly distributed in the individual stages and all stages can therefore be loaded to the maximum permissible pressure drop. In the described stepped gradation of individual components the last stage only contributes a relatively limited amount to the total capacity of the unit, which is advantageous for the overall useful percentage of total capacity. If breakthrough occurs in a stage when it is, for instance, 80% loaded, the unusable capacity is 20% of the installed capacity. In a two-stage installation in the aforementioned stepped gradation the second stage has 20% of the total capacity, the first stage is at 100%, the second stage 80% usable, so that only 4% of the total installed capacity is no longer usable. In a three-stage installation the unusable amount is reduced even further to 1% (77.1% of the total capacity in the first, 19.1% in the second and 4.8% in the last stage, 20% of which is unusable).

To improve breakthrough behavior, in the case of several parallel-connected housings the permeate streams are combined in the preceding stage before they are fed to the next stage. Since breakthrough of the target substance occurs in an adsorber module only in the last phase of loading, a particularly preferred form of series connection is a tandem installation. According to the invention, two identical stages A and B are used, in which either one is loaded and the other eluted or regenerated cyclically, or both are operated in series. The separation process then proceeds as follows.

Stage A is loaded with the liquid feed medium containing the target substance(s). Before the target substance in the permeate breaks through, the medium is fed to the freshly regenerated stage B. As soon as stage A is fully loaded, the remaining medium with buffer is rinsed from stage A into stage B and stage B, preloaded in this fashion, is then directly exposed to the medium, while stage A is eluted, so that the initial state, with interchanged stages, is achieved again. With control by a process controller, very short cycle times and thus very high separation efficiencies can be achieved. (Short cycle times are understood here to mean those of 15 minutes and less, whereas cycle times of several hours are usual with ordinary chromatography columns.)

Such an installation requires the use of a number of blocking and switching fittings so as to avoid the presence of "dead" or untraversed lines. An especially suitable system of membrane valves that combine a number of functions in a single component (up to 6 inputs with a bypass valve and flow reversal valves), and which has negligible dead volume is available from the MarcValve Corporation (Tewksbury, Mass.).

The invention is further explained below with reference to FIGS. 1 to 14 and the Examples.

To assist in understanding the invention by reference to the drawings, wherein like references generally refer to the same elements, a list of reference numbers and characters is provided below.

- 1 adsorption membrane
- 2 outer support element
- 3 inner support element
- 4 potting compound
- 5 upper end cap
- 6 lower end cap
- 7 bottom element
- 8 top element
- 9 housing outer wall
- 10 inner annular feed plenum
- 11 outer annular permeate plenum
- 12 feed inlet
- 13 permeate outlet
- 14 radial feed channels
- 15 core mandrel
- 16 vent
- 17 takeup assembly
- 18 threaded adjustment collar for takeup assembly
- 19 lower O-ring seal
- 20 upper O-ring seal
- 21 diffusion O-ring seals
- 22 core mandrel seal
- 23 clamping unit seal
- 24 threaded recess for connecting bottom element
- 25 upper core mandrel centering boss
- 26 lower core mandrel centering boss
- 27 cross-piece of upper end cap
- 28 connection flange of bottom element
- 29 lower connection flange of housing outer wall
- 30 upper connection flange of housing outer wall
- 31 connection flange of top element
- 32 feed distribution slopes
- 33 cleaning plenum
- 34 permeate distribution channel
- 35 centering boss O-ring groove
- 36 extension core
- 38 passage channels
- 39 spacers
- 40 body of connection piece designed in its upper part as a bottom element and in its lower part as a top element
- 41 sealing element
- 42 compressed air connection
- 43 upper external core threads
- 44 connection piece
- 45 adsorber module
- 46 male coupler
- 47 female coupler
- 48 core extension
- 49,50 housing outer wall seals
- 51 perforations
- 52 pin
- 53 groove
- 54 support frame
- 55–58 valves
- 59 bushing
- 60 radial connection channels
- 61 axial hole
- 62 sealing cone
- 63 closure element
- 64 threads
- 65 recess
- 66 holes for connection with interior of closure element 63
- 67 sealing element
- 68–109 on-off functions of valves
- 69 product discharge
- 96–98 bypass valves
- 100–102 bypass valves
- 89, 99 drain valve functions
- 103–117 direction reversal valve functions
- pA1, pA2, pB1, pB2, pM, pR pressure measurement devices
- UVA, UVB UV extinction coefficient monitors
- LA, LB conductivity monitors
- LDM, LDE air detectors for protection against pumps running dry
- PM, PE pumps
- DM, DR volume measurement units
- FA, FB, FR prefilter units
- 4A, 4B back pressure valves
- 5A, 5B drain valve functions
- 1A, 1B, 3A, 3B venting valve functions
- 6A, 6B bypass opening valve functions
- 14A, 14B, 15A, 15B flushing valve functions
- 118 local static pressure in feed plenum
- 119 local static pressure in permeate plenum
- 120 local static pressure difference between feed and permeate plenums
- 121 tube
- 122 riser
- 123 sealed annular cavity
- 124 closure part
- 126 feed manifold
- 127 permeate manifold
- 128 center column
- 129 rinsing line
- 130 vent line
- 131 supply part
- 132 vent and rinsing connection
- 133 fill tube
- 134 compressed air supply In an exemplary embodiment I of the apparatus according to the invention depicted in FIG. 1, a bottom element 7 is connected to a support frame (not shown) by fastening means such as a bolt into recess 24, and a core mandrel 15 is positioned with its lower recess on lower core mandrel centering boss 26 of element 7. A cylindrical spiral wound adsorber module 45 is mounted from the top onto core mandrel 15, so that radial flange 27 of upper end cap 5 snugly abuts a corresponding shoulder on core mandrel 15. The elements designated with reference numbers 28, 29 and 30, 31 represent connection flanges. Although their design is not shown in detail in FIG. 1, they are preferably connections known as "aseptic connectors" which are machined precisely to form an O-ring groove to accept diffusion O-ring seals 21 to prevent diffusion of the liquid medium to be filtered.

Housing outer wall 9 is connected to bottom element 7 via flanges 28 and 29. Top element 8 is mounted to housing outer wall 9 by takeup assembly 17 having threaded adjustment collar 18 loosely fitting into top element 8. After mating connection between flanges 30 and 31, threaded adjustment collar 18 of takeup assembly 17 is tightened, creating axial clamping pressure between top element 8 and housing outer wall 15. Takeup assembly 17 assures the axial sealing pressure required for sealing engagement of diffusion O-ring seals 21, even in the event of manufacturing tolerances in the lengths of core mandrel 15 and housing outer wall 9. Diffusion O-ring seals 21 do not have to withstand any pressure load due to the sealing action created by the higher hydrostatic pressure in inner annular feed plenum 10 relative to the pressure in outer annular permeate plenum 11, which causes sealing by lower O-ring seal 19 and upper O-ring seal 20 of adjacent inner annular feed plenum 10, and by core mandrel seal 22. 0-ring seals 21 instead have the task of preventing diffusion of liquid into the gap between upper end cap 5, core mandrel 15, and takeup assembly 17, as well as between lower end cap 6, core mandrel 15 and bottom element 7.

It should be noted that instead of threaded adjustment collar 18, compressed air can also be used to apply the axial sealing force, whereby takeup assembly 17 is designed, in principle, as a pneumatic cylinder. This variant is particularly preferred for larger installations, wherein a multiplicity of adsorption modules are called for. When such an embodiment is incorporated, compressed air may be used for purging and cleaning the apparatus. Another advantage of such an embodiment comes into play if different temperatures occur during operation of the device-for example, with the use of hot cleaning media. The pneumatic application of the axial sealing force means that the different expansion coefficients of the housing outer wall and the core mandrel are compensated for. Another way to accommodate different expansion coefficients would be to provide a spring element between threaded adjustment collar 18 and takeup assembly 17.

Fluid connections and fittings to feed inlet 12 and permeate outlet 13 are made after fabrication of the device. To remove air from the device, the device is initially filled with a rinsing medium such as a buffer solution via permeate outlet 13 while vent 16 is opened. When all air has been exhausted from the device, vent 16 closed and the rinsing medium fill is continued until feed inlet 12 is flooded. Loading of the adsorbtion separation device with liquid feed through feed inlet 12 can then take place, during which time introduction of air must be avoided. To this end, an air bubble detector/separator is preferably provided in the plumbing for the device.

Another fitting preferably used in connection with operation of the device includes a back pressure valve mounted downstream of permeate outlet 13, which ensures that the medium in the device is always under a certain excess pressure (preferably 0.2 to 0.7 bar) under operating conditions. Separation of gas bubbles in the pores of the adsorption membranes is also prevented by this means. Without excess pressure of the liquid medium in the device, there is a hazard that in cases where the medium has a supersaturation of dissolved gases, these gases can accumulate in the pores of the membrane(s) and ultimately adversely affect both flux and adsorption capacity of the device. For prevention of supersaturation of the medium with dissolved gases without a back pressure valve, it may be helpful to heat a medium that has been saturated with air at room temperature during operation, for example, by pumping the medium.

The liquid medium to be treated flows from feed inlet 12 through radial feed channels 14 into inner annular feed plenum 10 via feed distribution slope 32. Feed distribution slope 32 causes substantially rotationally symmetric flow distribution of the medium and substantially uniform pressure distribution. After radially outward flow of the medium through adsorption membrane 1, the permeate flows through the outer annular permeate plenum 11 via sloping permeate distribution channel 34 to permeate outlet 13. Cleaning plenum 33 functions to distribute liquid from outer annular permeate plenum 11 when vent 16 is activated to flush the upper regions of the annular permeate plenum. O-ring groove 35 has no utility in the case of a single adsorption module. However, it does permit the stacking or telescoping of additional core mandrels and adsorption modules, such as shown in FIG. 2.

Figure 2:
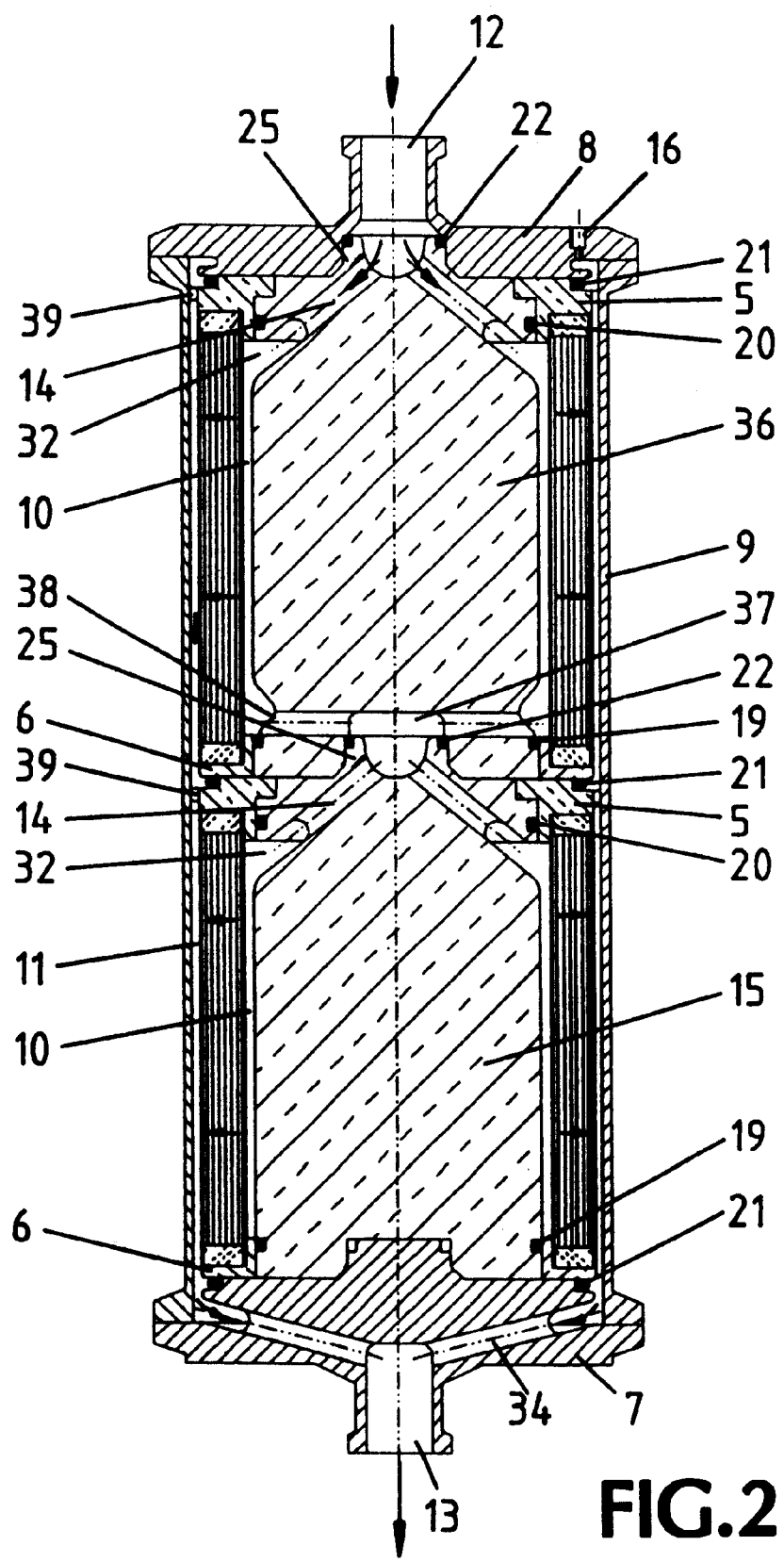
FIG. 2 is a vertical section through an exemplary embodiment I-type device of the invention with two parallel-connected spiral wound adsorber modules with the same number of windings in a common housing.

Another exemplary design of the device of the invention utilizing embodiment I is shown in FIG. 2, wherein two adsorber modules are connected in series in a common housing; to aid in understanding, takeup assembly 17 is not depicted. Instead of the integral housing shown in FIG. 2, it is also possible to assemble the housing from multiple parts when there are more than two adsorber modules in a housing. Core extension mandrel 36 differs from core mandrel 15 only in its lower part, namely, by the presence of radial indents forming passage channels 38, which permit passage of the liquid feed medium from the inner annular feed plenum 10 of the upper module into the inner annular feed plenum of the lower module. Outer annular permeate plenum 11 is common to both modules. Spacers 39 may be molded onto upper end cap 5, or onto potting compound 4 that can be produced via a corresponding casting mold; their function is lateral support of the adsorber modules in the housing.

A connector for series connection of adsorber modules in an apparatus of embodiment I of the invention is shown in detail in FIG. 3. The body 40 is designed in its upper part as a bottom element and in its lower part as a cover element, and is connected to the upper portion of housing outer wall 9 via flange 28 to the lower portion of housing outer wall tube via flange 31. Permeate from the upper stage is fed from its outer annular permeate plenum to the inner annular feed plenum of the next or lower stage through distribution channels 34. A vent in the venting unit 16 is arranged here on the side. Pressure for the takeup assembly 17 is applied pneumatically via compressed air connection 42. The region exposed to compressed air between the body 40 and takeup assembly 17 is sealed by seals 23 and 41.

Figures 4A, 4B, 4C:
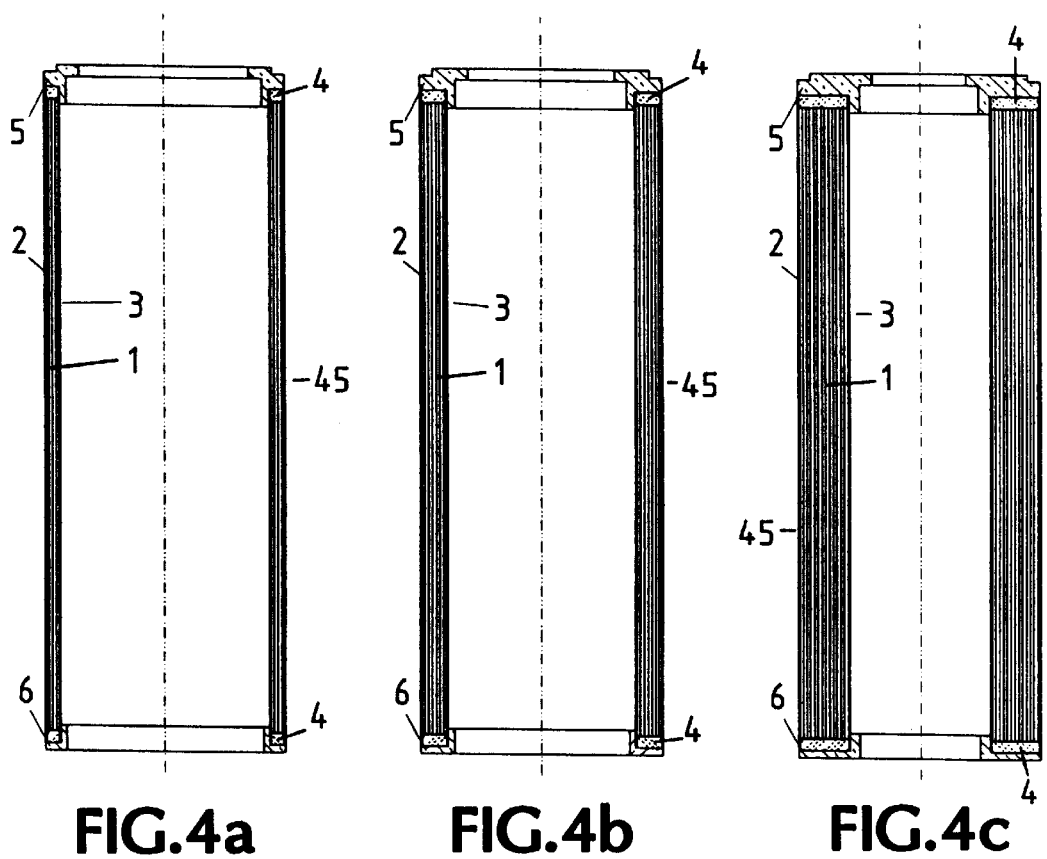
FIGS. 4a–4c are vertical sections through adsorber modules according to the invention with varying numbers of windings.

Referring to FIGS. 4a–4c, the cylindrical spiral wound adsorber modules 45 of the invention consist of windings with a widely varying number of wraps of adsorption membrane 1, lower end cap 6, upper end cap 5, potting compound 4 to embed the adsorption membrane into end caps 5 and 6, and, in a preferred embodiment, an inner support 3 and an outer support 2, both supports being permeable to liquids.

An entire system of embodiment I-type devices may consist of a wide variety of adsorption modules. For example, modules 45 may be of five length gradations (3.1, 6.25, 12.5, 25 and 50 cm) and four gradations of numbers of windings (8, 15, 30 and 60) of adsorption membranes 1, as exemplified in FIGS. 4a–c. The resulting different wall thicknesses of module 45 with 8 and 15 windings may be compensated for in the former case by additional layers of spacer 39 (not shown). Bottom element 7, top element 8, and housing outer wall 9 are the same for the three numbers of windings depicted in FIGS. 4a–c. Thus, it may be seen that the invention also contemplates a modular system which permits the assembly of 20 different configurations with a minimum of different components. For example, the modules can be used in the device in accordance with embodiment I, as well as in accordance with embodiments II, III and IV (discussed below). Because of the great degree of flexibility offered by the separation devices of the present invention, a broader size range of separation devices may be attained, that may be made identical in terms of flow rates or flux. This feature permits reliable preliminary studies during scale-up of technical processes. Exemplary combinations of modules are set forth in Table 1.

TABLE 1

| Number of Windings | Surface Area of Individual Modules 3.1 cm Long | Surface Area of Three 50 cm Long Modules |
|---|---|---|
| 8 | 625 cm$^2$ | 3 m$^2$ |
| 15 | 1250 cm$^2$ | 6 m$^2$ |
| 30 | 2500 cm$^2$ | 12 m$^2$ |
| 60 | 5000 cm$^2$ | 24 m$^2$ |

Figure 5:
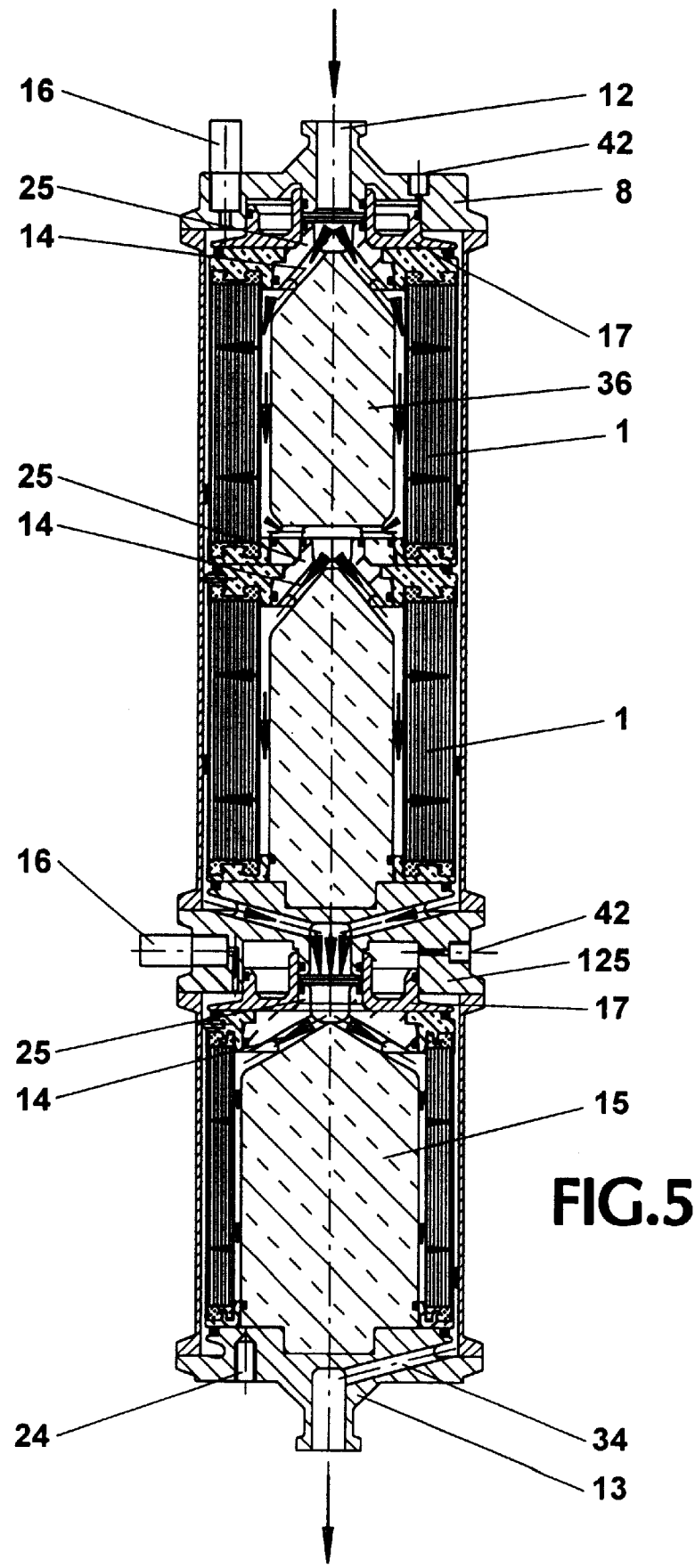
FIG. 5 is a vertical section through an exemplary apparatus of the invention with two spiral wound adsorber modules in tandem and having the same number of windings in a common housing, these in turn being connected in series with a second module in a second housing, the second module having fewer windings.

The incorporation of the connector shown in FIG. 3 in a two-stage installation using embodiment I-type devices is shown in FIG. 5, wherein the first stage consists of two identical spiral wound adsorber modules and the second stage of an adsorber module with half the number of windings. This arrangement is viewed as a lab scale installation. As is apparent to one skilled in the art, three- and multi-stage installations can be assembled according to the same principle, wherein the height of the installation is the only limiting factor.

Figure 6:
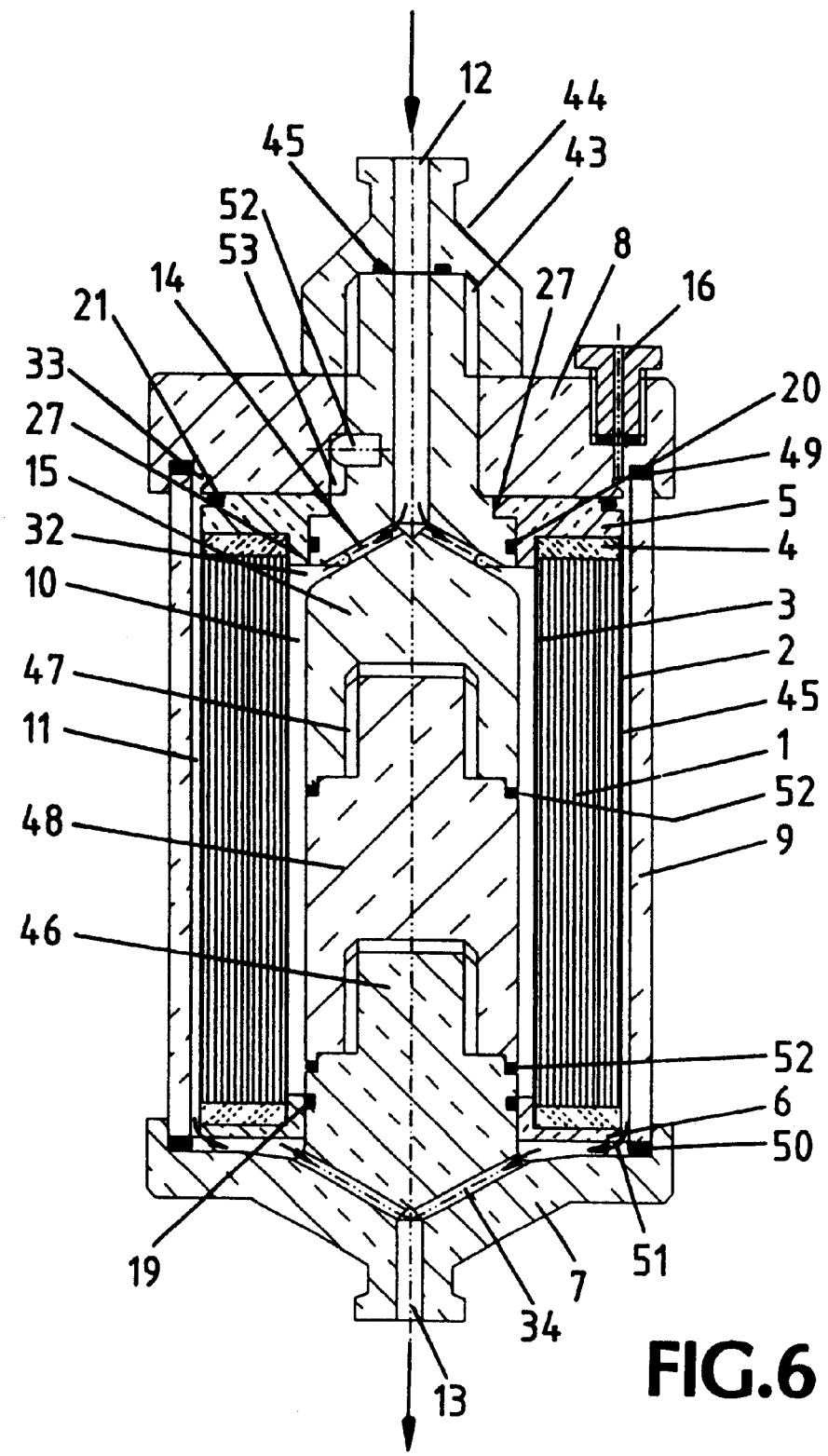
FIG. 6 is a vertical section through another exemplary separation device of the invention denominated as embodiment II.

The adsorber module 45 in embodiment II depicted in FIG. 6 is of substantially similar design to the module of embodiment I. Core 15 is connected by female coupler 47 on the bottom to male coupler 46 of bottom element 7 via core extension 48. Core extension 48 can have different lengths, so that modules of different lengths can be used. Housing outer wall 9, accordingly, has different lengths. The dimensions of core extension 48, bottom element 7, core mandrel 15 and housing outer wall 9 are chosen so that adsorber modules can be used in the length gradations of, for example, 50, 25, 12.5 and 6.25 cm, in which core extension 48 drops out entirely for the shortest unit and core mandrel 15 is secured directly to bottom element 7. Core mandrel 15 may be provided with external threads 43 on its top, onto which a connection piece 44 is secured, which fastens top element 8. Housing outer wall 9 is clamped between bottom element 7 and top element 8 so that outer annular permeate plenum is sealed by means of housing outer wall seals 49 and 50. Pin 52 engages groove 53 in top element 8, and prevents rotation during tightening of connection piece 44 on threads 43. Cross-piece 27 of upper end cap 5 is clamped between top element 8 and core mandrel 15, thereby applying pressure to diffusion inhibition seal 21. The permeate flows around lower end cap 6 and is discharged via permeate distribution channel 34. The groove of the lower housing outer wall seal 50 has perforations 51 on the inside in order to prevent collection of more dense liquids in the groove. Diffusion inhibition seals 52 prevent penetration of liquid into the coupling elements 46 and 47, so that contamination is avoided.

Figure 7:
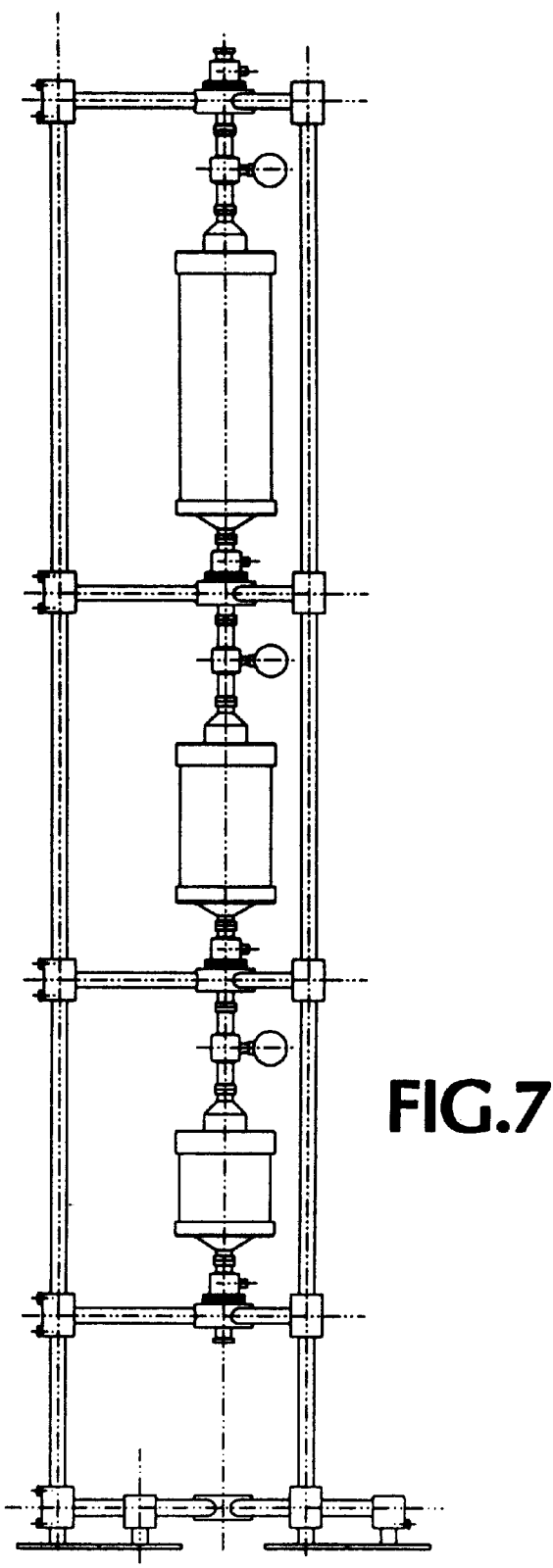
FIG. 7 is a schematic depicting the arrangement of an exemplary three-stage series connection of embodiment II-type devices of the invention.

FIG. 7 shows an exemplary arrangement with three embodiment II-type filtration devices connected in series on an appropriate mounting frame, with pressure gauges interposed before each feed inlet. When housing outer walls are fabricated with Plexiglas, such an arrangement permits the adsorptive separation processes to be observed visually during multistage operation.

Figure 8A:
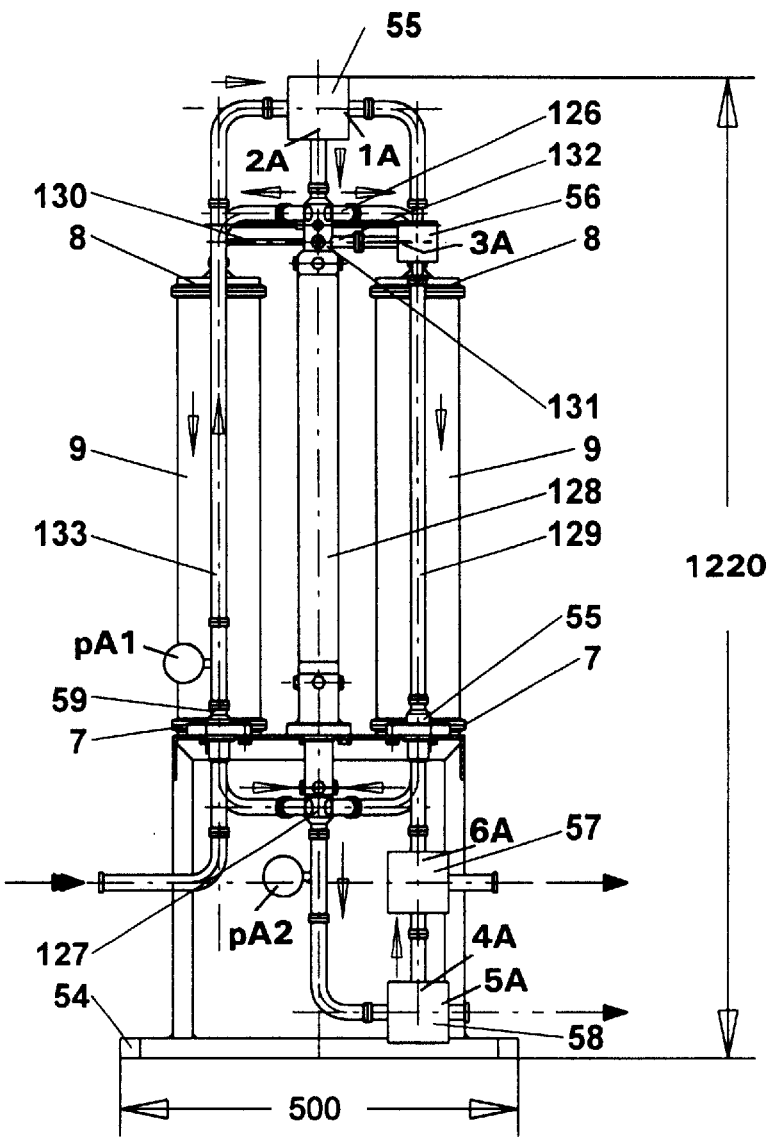
FIGS. 8a–8b are vertical and plan sections respectively, of an adsorptive separation stage consisting of four embodiment I-type devices connected in parallel, each in its own housing, drawn to scale with dimensions in millimeters.
Figure 8B:
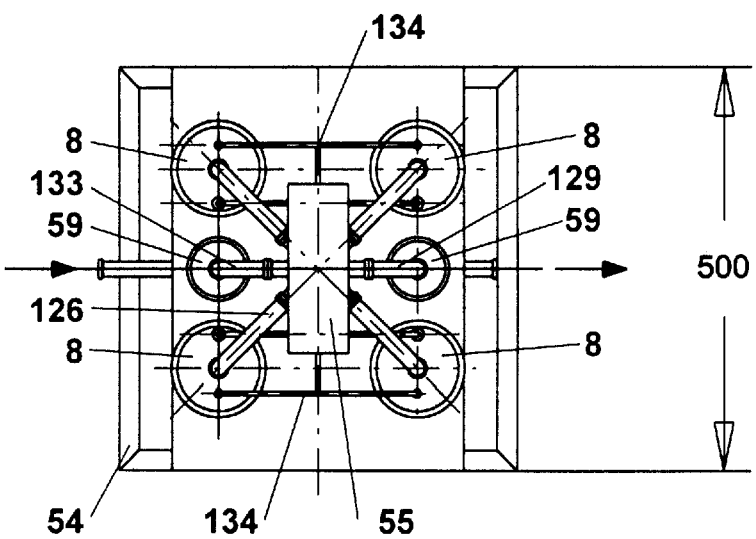

FIGS. 8a and 8b comprise a depiction, true to scale, of a vertical section and plan view of a filter array of four adsorber filtration devices of the design of embodiment I mounted together on a support frame 54. The four devices are connected in parallel via feed manifold 126 on the inflow side and via permeate manifold 127 on the outflow side, and can therefore be used as a single stage of a tandem installation or as a multi-stage installation. With lower capacity requirements this arrangement-which represents the basic unit of the scale-up system according to the invention-can, of course, be operated as an independent installation. Valves 55, 56, 57 and 58 are pneumatically controlled diaphragm valves and serve to control filling and venting of the unit. Fill tube 133 and venting and flushing line 129 are attached to support frame 54 by bushings 59. Top elements 8 correspond in design to the pneumatic pressure of the clamping unit 17, as shown in detail in FIG. 6. Feed manifold 126, compressed air supply 134 and vent lines 130 are combined into an integral part 131, from which the venting and rinsing connection 132 leads to valve 56. Supply part 131 is attached to center column 128 in such a manner that it can be fixed in a position that is rotated toward the axis of the center column during assembly, for example, during a module change of modules. The same is true for permeate manifold 127 on the outflow side. Valve 58 allows for drainage of the filter array during shutdown.

FIGS. 9a and 9b show an exemplary further scale-up of the invention, using the array depicted in FIGS. 8a and 8b mas the first stage and modules of the type depicted in FIG. 2. A three-stage array with 3 modules in each of four housings for a total of 12 modules in the first stage, 3 modules in 2 housings for a total of 6 in the second, and 3 modules in a single housing in the third stage is shown drawn to scale, which corresponds to 96 m$^2$, 24 m$^2$ and 6 m$^2$, i.e., a total of 126 m$^2$ membrane surface area. The required "footprint" or ground surface area is less than 1 m$^2$, with a construction height of slightly less than 2.3 m. As is apparent to one skilled in the art, parallel connection is not limited to four individual units and, in large installations, several groups of four can also be parallel-connected within stages, if symmetry in the plumbing is maintained. This symmetry and the resulting equalize pressurization caused by it is important for optimal results. A desirable feature of the invention is that it enables one to design industrial installations utilizing known basic studies and furthermore readily lends itself to scaling up while at the same time permitting custom engineering of individual modules and components.

Figure 10:
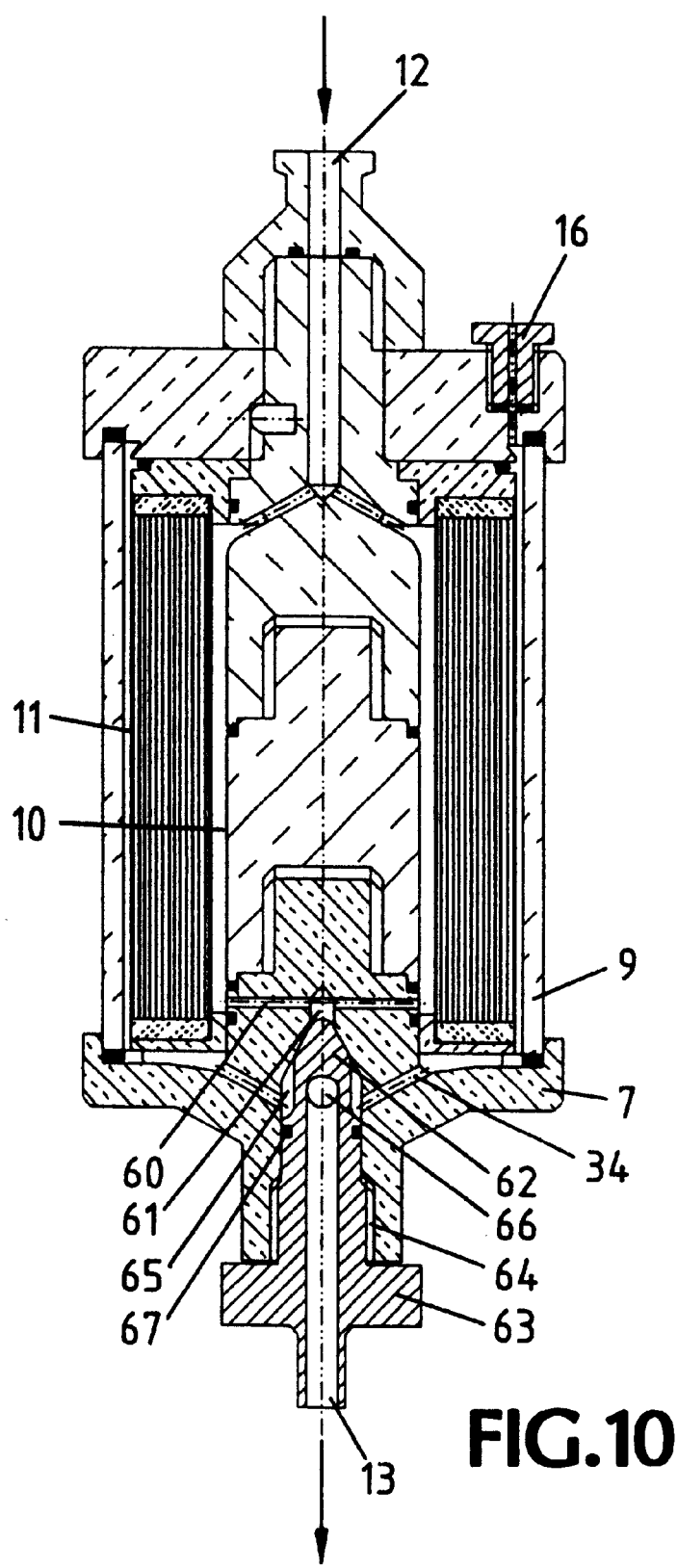
FIG. 10 is a vertical section through another exemplary device of the invention denominated as embodiment III.

FIG. 10 shows a further exemplary embodiment III for cross flow operation, wherein only the bottom element 7 is changed relative to embodiment II. In embodiment III bottom element 7 is modified so as to have radial connection channels 60 connect inner annular feed plenum 10 to an axial hole 61, which may remain partially open or is closable by sealing cone 62. Sealing cone 62 is situated on closure element 63, which threadingly engages bottom element 7 by threads 64. Closure element 63 has a recess 65 that leaves a free space between it and bottom element 7, and into which space permeate distribution channels 34 from outer annular permeate plenum 11 discharge. Closure element 63 also has holes 66 in the region of the recess 65, through which liquid reaches its interior and can flow out via axial permeate outlet 13, which may be designed as a hose nozzle. The region of the recess 65 is sealed on its outer portion by sealing element 67. The amount and ratio of liquid flowing from inner annular feed plenum 10 and outer annular permeate plenum 11 may be varied by turning closure element 63, which in turn varies the degree of opening of sealing core 62. In this embodiment the medium to be filtered and the permeate are not withdrawn separately, but rather are remixed within the apparatus, so only a single discharge is required. A target substance-containing particle suspension is supplied and a particle suspension is withdrawn, depleted in the target substance. For complete adsorption of the target substance, the suspension can be recirculated.

Figure 11:
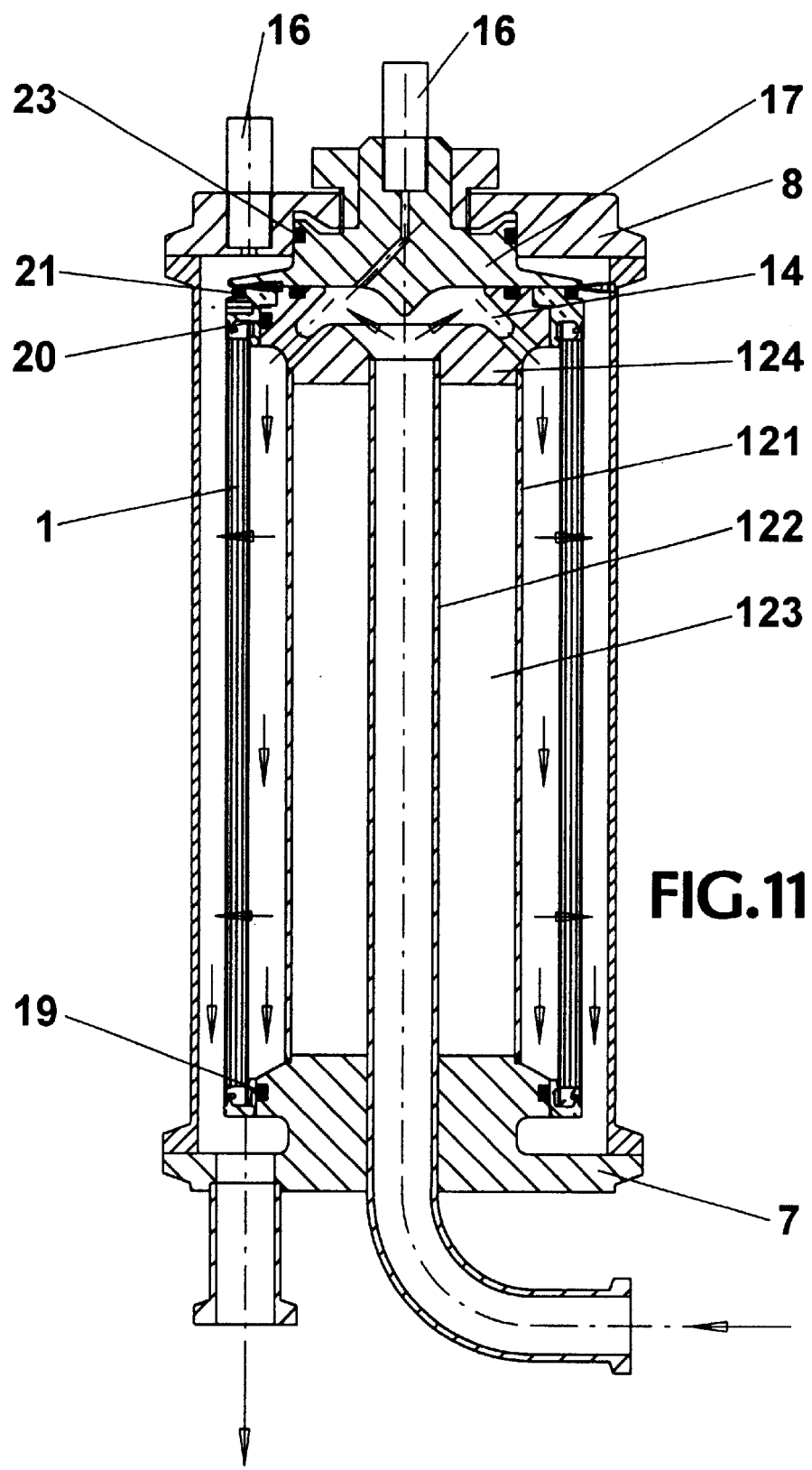
FIG. 11 is a vertical section through another exemplary device of the invention denominated as embodiment IV.

FIG. 11 shows yet another exemplary embodiment of the invention, denominated embodiment IV, which is preferably fabricated from steel, typically utilizing housings of the type that are commonly found in conventional pleated filter cartridges, with the exception that the flow direction is from the inside to the outside and it therefore has two vents 16. The core, formed a tube 121 and a closure part 124, is welded to the bottom plate and contains a riser 122 in the interior. Bottom plate 7, tube 121, riser 122 and closure part 124 together form a tightly sealed annular cavity 123. Closure part 124 and the takeup assembly 17 are so fabricated as to form a bend, which causes mild deflection of the liquid feed stream. Closure part 124 contains distribution channels 14, which discharge at a steep angle into inner annular feed plenum 10, thereby minimizing potential adverse effects arising from a dynamic pressure directed at adsorption membrane 1.

Figure 12A:
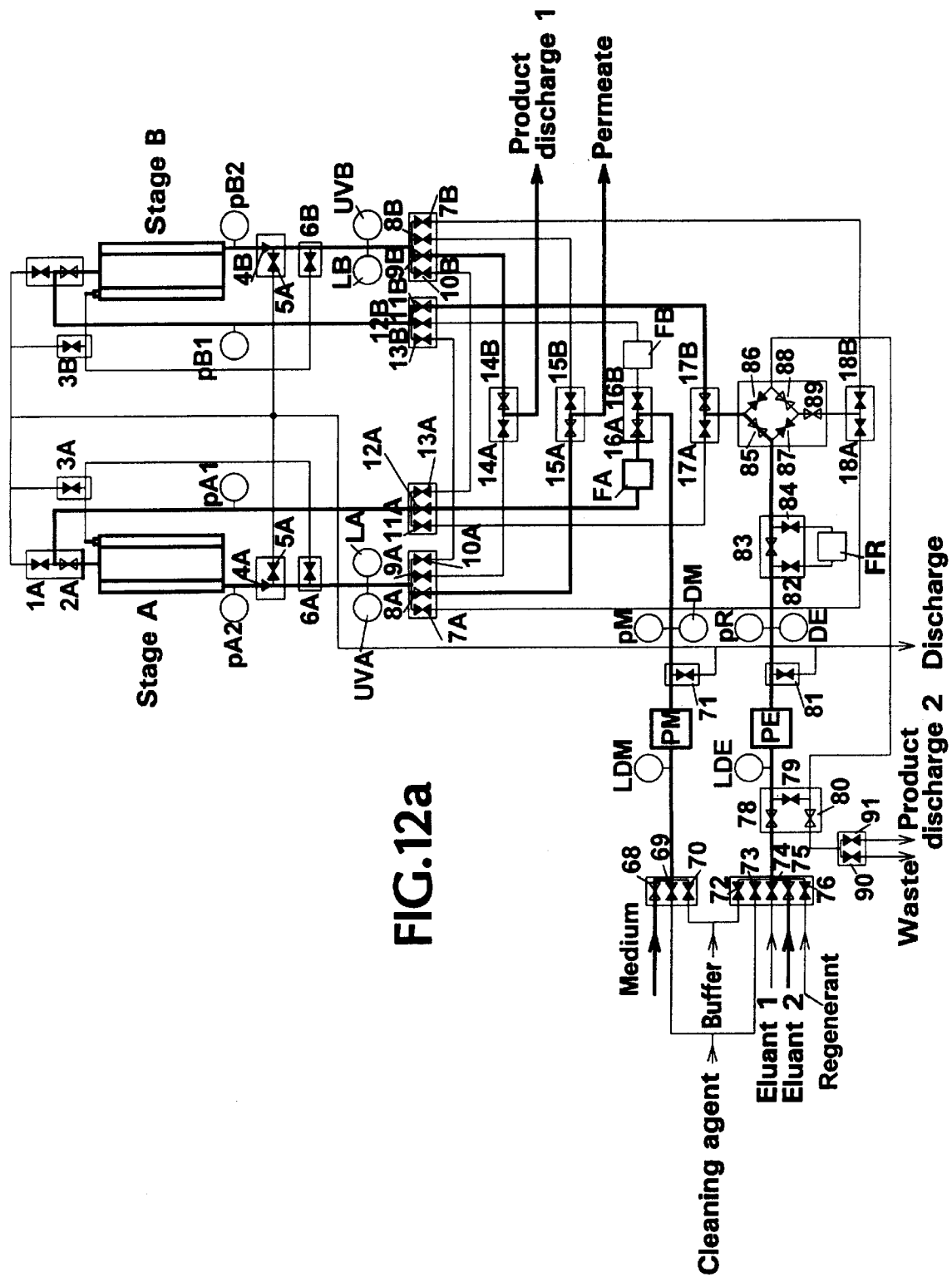
FIGS. 12a–12c are schematics of a flow chart of a tandem installation according to the invention.
Figure 12B:
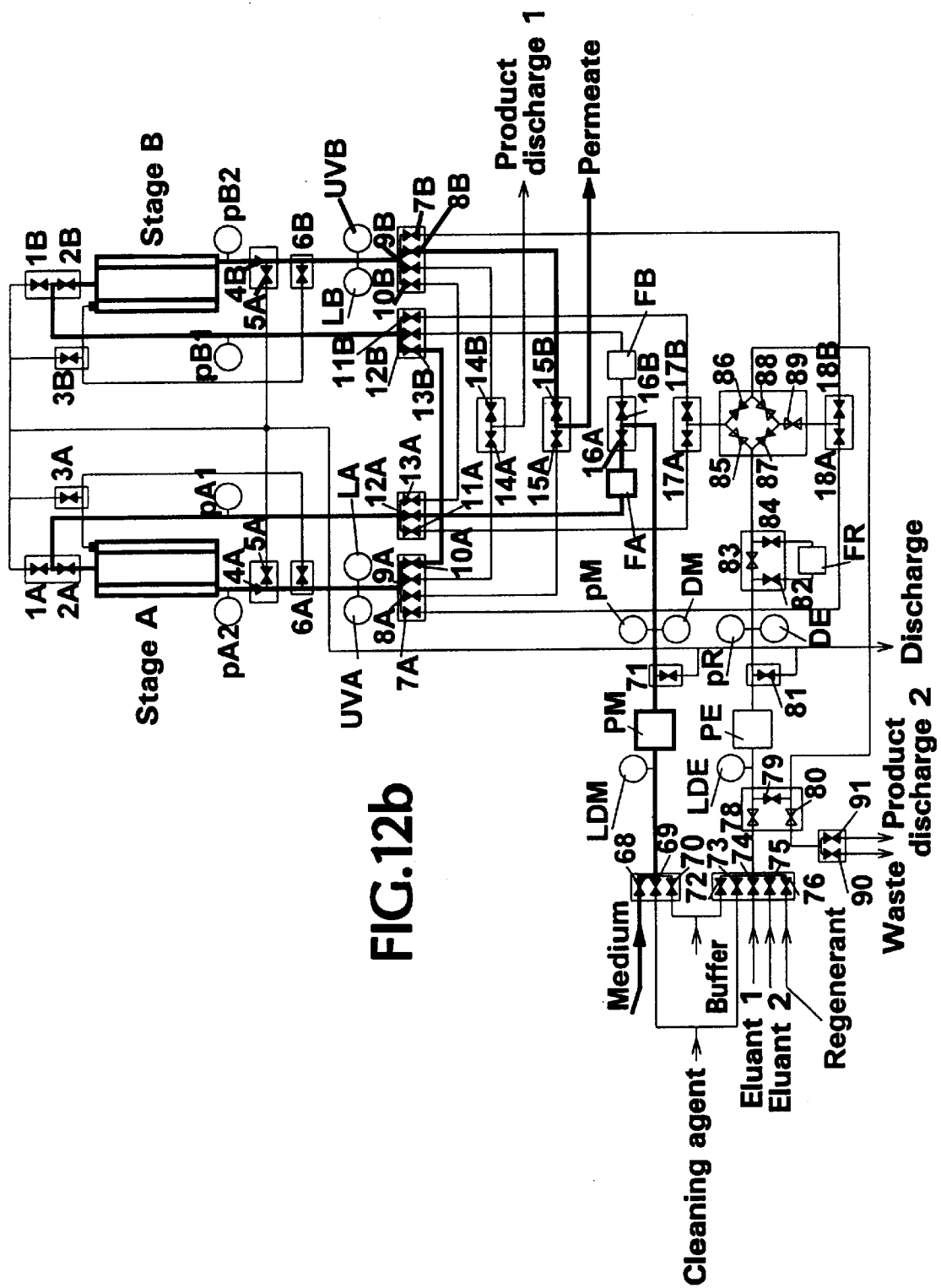
Figure 12C:
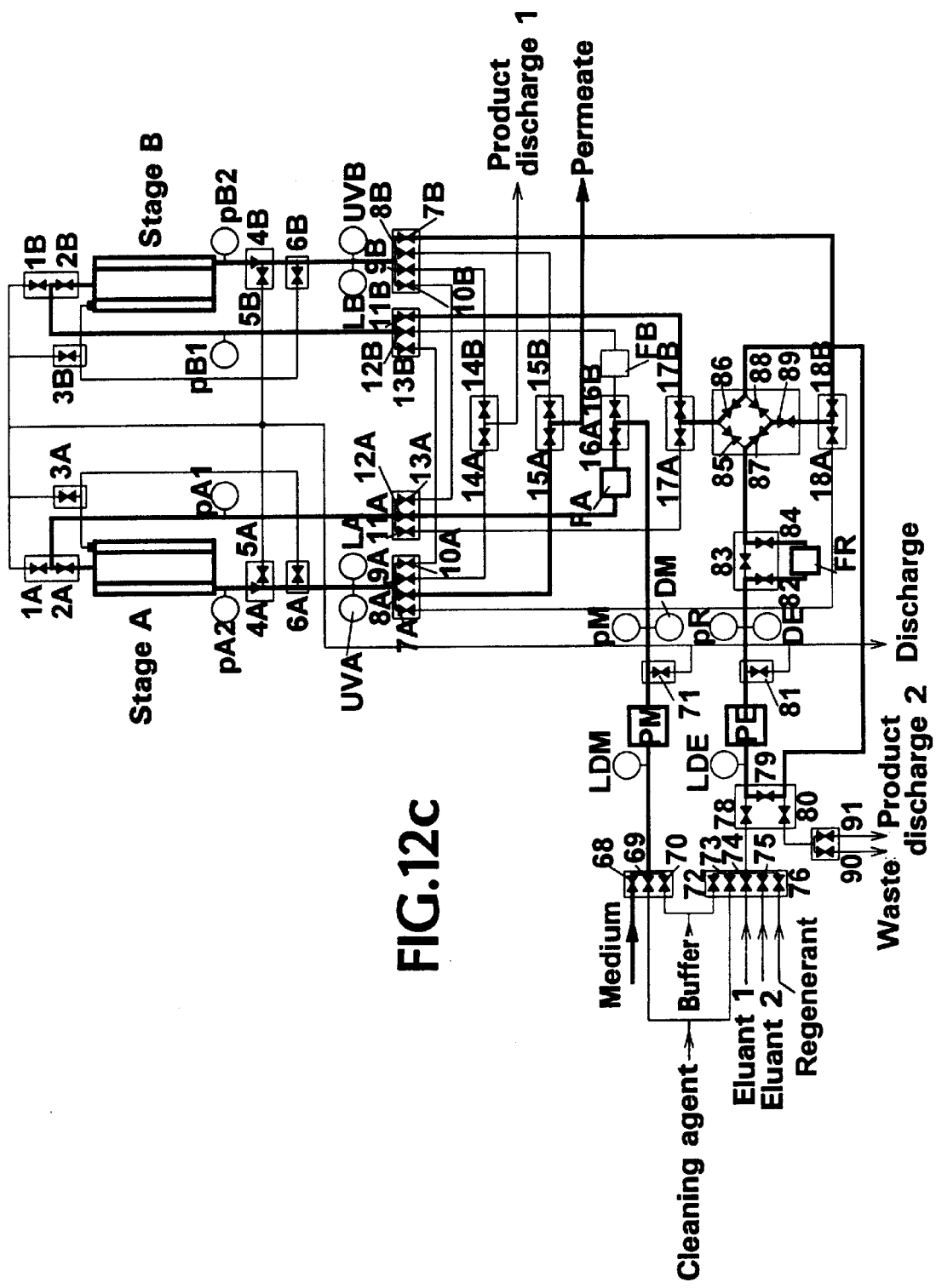

A flow chart of a tandem installation is shown in FIGS. 12a–12c. This is a variant for two-stage elution wherein a first bound contaminant is eluted with eluant 1, followed by the elution of a second bound contaminant with eluant 2 (or vice versa). Stages A and B are identical adsorber units, which consist either of a single module or of parallel- and/or series-connected individual modules; pA1, pA2, pB1, pB2, pM, pR are pressure measurement devices; UVA and UVB are monitors to determine UV extinction coefficients; LA and LB are conductivity monitors; LDM and LDE are air detectors for protecting the pumps from running dry; PM and PE are pumps; FA, FB and FR are prefilter units; and the numbers 68 to 109 denote individual open-close functions of the valves, wherein valve functions with identical tasks have the same numbers in the two stages and are distinguished by the additional stage designations A or B. Valves with valve functions 96 to 98 and 100 to 102 are bypass valves; valve functions 4A and 4B are back pressure valves; valve functions 5A, 5B, 89 and 99 control drain lines; valve functions 1A, 1B, 3A and 3B control ventilation; 6A and 6B open a bypass from the ventilation unit of the module; and valve functions 103 to 117 provide for direction reversal.

FIG. 12a shows an installation wherein stage A is exposed to the medium bearing the substances to be separated, while the product is eluted from stage B. FIG. 12b shows exposure of stages A and B to the medium in series. FIG. 12c, on the other hand, shows options obtainable from the functional valve layout. While stage A is exposed to the medium, regeneration occurs in stage B in a closed loop via back flushing. The regenerant filter—whose bypass is closed to all other liquids—is then connected into the loop so that particulate contaminants that can be released by the adsorber do not become redeposited.

The circulation circuit is also usable with other liquids conveyed by pump PE and in both directions. For example, it is also possible to circulate eluant 2, which, in the subject application, causes elution of the product. In this case, the product situated in the tube system of the circuit is then rinsed from the system with buffer via the product discharge 69. For simpler applications, back flushing may be dispensed with, so that use of the direction reversal valve (valve functions 101 to 107) is unnecessary. In cases wherein the permeate is considered the product, when contaminants are to be removed from the medium, the product discharge lines shown and the corresponding fittings can be dispensed with. The valve functions (for example, 14A, 14B and 15A, 15B) wherein the same liquid is always situated on both sides (product and permeate) primarily serve for effective flushing, because they permit separate flushing of the stages without the possibility of contamination of the lines used from the unflushed lines.

Figure 13A:
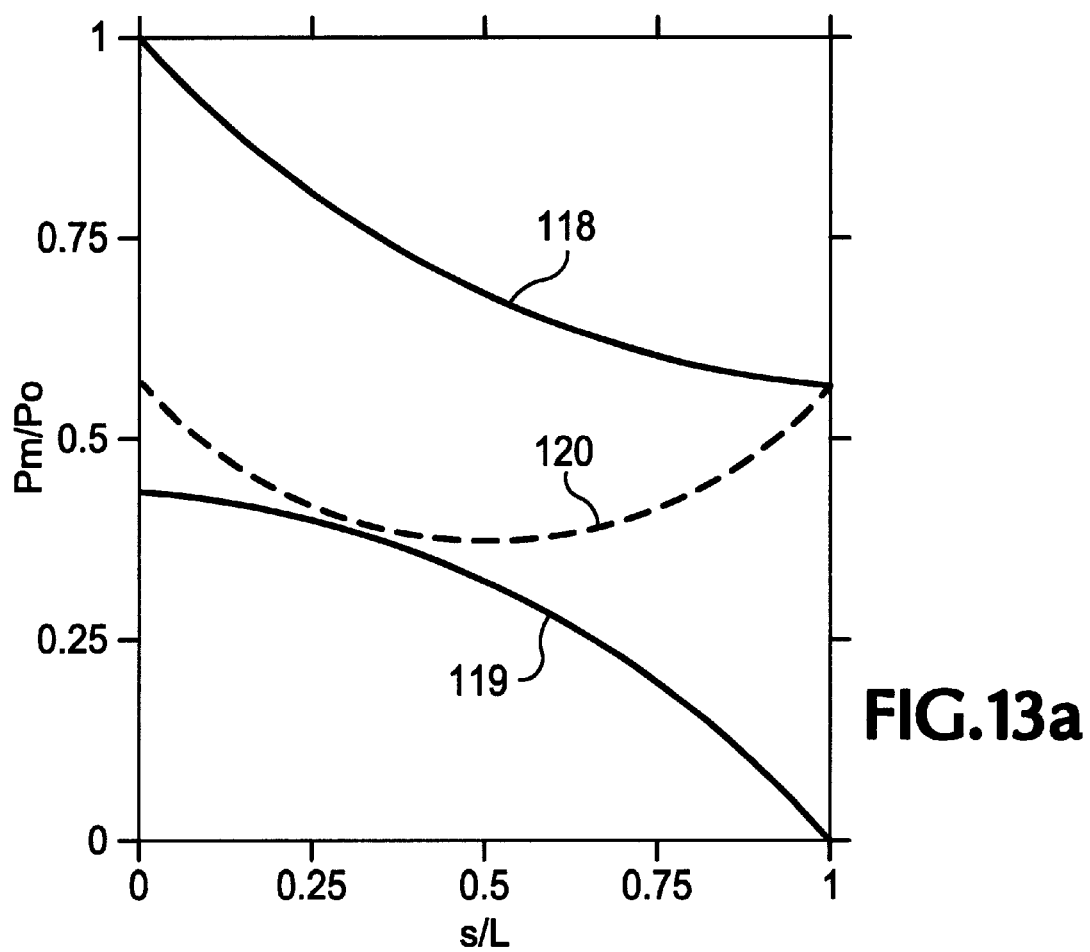
FIGS. 13a–13c graphically depict the relations between a dimensionless resistance parameter A and local static pressures in the annular plenums of the device of the invention, as well as the adsorption capacity of the device.
Figure 13B:
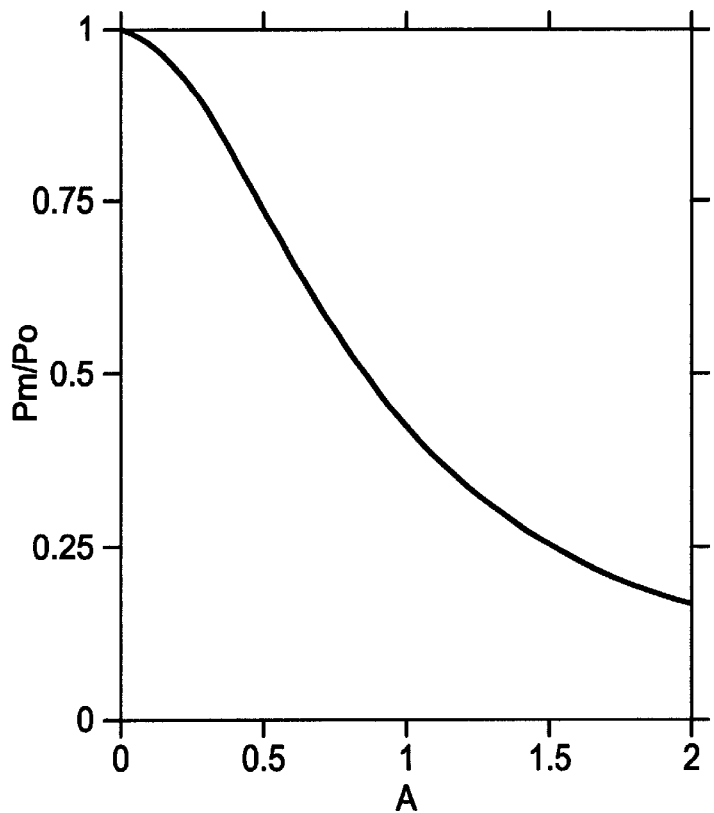
Figure 13C:
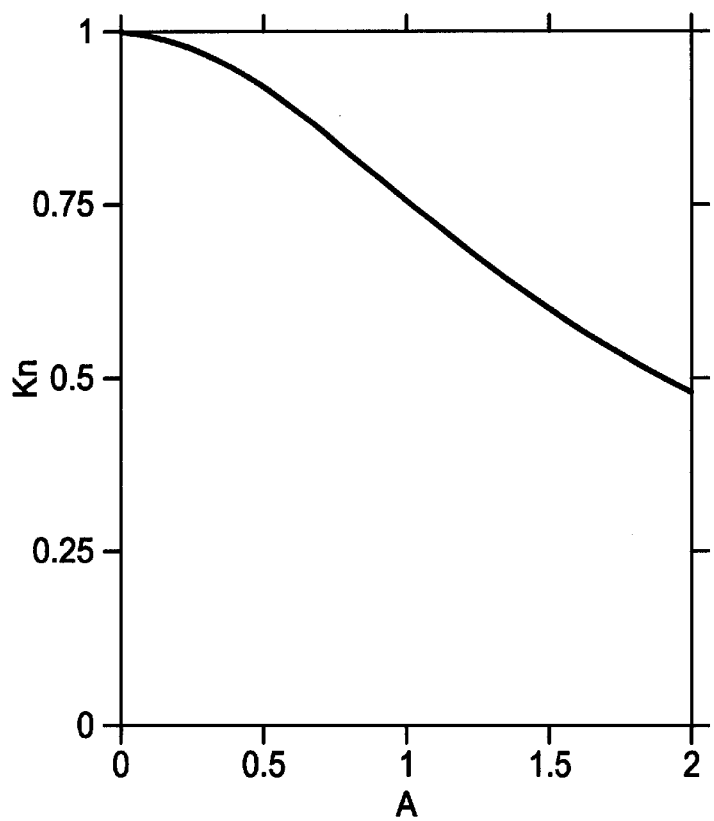

FIG. 13a is a graph plotting the relationship between local static pressure 118 in the annular feed plenum, the local static pressure 119 in the annular permeate plenum (during free discharge), and the local pressure difference 120 when the dimensionless resistance parameter A=1, wherein s denotes the length of the zone from feed inlet 12 to annular feed plenum 10 (see FIGS. 1–2). The average pressure difference as a function of A is shown in FIG. 13b, while the loss-free utilization capacity as a function of A is shown in FIG. 13c.

According to the invention, devices are preferred wherein the dimensionless resistance parameter A is less than 0.2 according to the above calculation, and more preferably less than 0.1. To achieve minimal dead volumes, a value of approximately 0.02 is preferred as a lower limit for A.

EXAMPLE 1

Concentration of Hemoglobin with a Strongly Acid Membrane Adsorption

Four volumes of fresh bovine blood were mixed with 1 volume of an aqueous solution of 3.8% trisodium citrate and 0.9% sodium chloride, centrifuged for 10 minutes at 3000 g, the supernatant decanted, the erythrocytes sediment hemolyzed with ten-fold volumes of deionized water, filtered in cross-flow through a 0.2 $\mu$m microfiltration membrane, and the hemoglobin (Hb) content of the permeate determined with the Drabkin reagent relative to a standard (both from Sigma Deisenhofen).

The permeate was adjusted to a pH of 6.0±0.05 with potassium phosphate and deionized water, to an ionic strength of 5 mM and a Hb content of 3 mg/mL, and then pumped through an embodiment I-type apparatus with a strongly acid adsorption membrane of the type disclosed in U.S. Pat. No. 5,547,575 having 8 $m^2$ surface area and 60 windings, until the characteristic UV extinction coefficient for Hb in the permeate reached 10% of that of the initial feed solution. This occurred after a volume throughout of 33 L.

After rinsing until achievement of the baseline, elution was carried out with a 0.1 M solution of buffered potassium chloride, the eluate was trapped in fractions of 0.2 L, and the Hb content determined. The values obtained are shown in Table 2.

TABLE 2

| Fraction Number | Concentration Hb [mg/mL] | Total Hb [g/fraction] |
| --- | --- | --- |
| 1 | 0.0 | 0.00 |
| 2 | 2.04 | 0.41 |
| 3 | 27.2 | 5.54 |
| 4 | 80.2 | 16.04 |
| 5 | 87.4 | 17.84 |
| 6 | 84.9 | 16.98 |
| 7 | 58.3 | 11.66 |
| 8 | 38.2 | 7.64 |
| 9 | 12.7 | 2.54 |
| 10 | 7.4 | 1.48 |
| 11 | 4.6 | 0.92 |

The Hb yield over all fractions was very good at 81.4%, and was 76.1% over fractions 3–8. Concentration over fractions 3–8 was 20-fold, and in peak fractions 5 and 6 was 28-fold.

EXAMPLE 2

Separation of Endotoxin From a Pyrogen-containing Solution with a Strongly Basic Adsorption Membrane An adsorptive separation device of substantially the same design as embodiment II was used, equipped with a strongly basic adsorption membrane of the type disclosed in U.S. Pat. No. 5,547,575. The number of windings of the adsorption membrane material in the spiral wound adsorber module was 30, and the total membrane surface area was 1 m². The device was first exposed to 2 L of 1 M sodium hydroxide to remove any pyrogens present and, after 60 minutes, rinsed with 5 L of buffer solution. A pyrogen test using Limulus Amoebocyte Lysate with a sensitivity of 6 pg/mL showed the absence of pyrogens.

Twenty L of a solution of 0.5 g/L γ-globulin fraction from cattle (Sigma Deisenhofen) and 100 ng/mL in 0.05 mol/L potassium phosphate buffer (pH 6.0) were pumped through the device over a period of 10 minutes, and the protein concentration in the permeate was determined and tested for endotoxin. Protein concentration was shown to be 0.48 mg/mL and the pyrogen test was negative, corresponding to an excellent logarithmic reduction value (LRV) of >3.5.

EXAMPLE 3

DNA Depletion

The initial feed stream comprised the process stream of a multistage process for monoclonal antibodies from a cell culture of mammal cells that had been prepurified via a protein-A column from Pharmacia. The process stream leaving this column amounted to 550 to 650 L containing between 640 and 766 g of antibodies and between 67 and 370 picograms of DNA per mg of antibody according to an enzymatic Threshold Analyzer from Molecular Devices of Menlo Park, Calif. This process stream was fed through an adsorptive separation unit having the design of embodiment I with 15 layers (2 m²) of a strongly basic ion exchange membrane at a flow rate of about 5 L/min. The effluent leaving the unit had a DNA content of less than 5 picograms per mg of antibody, indicating virtually complete removal of the DNA target substance.

EXAMPLE 4

Improvement of Breakthrough Curves by Adsorber Modules in Series

Hemoglobin concentration was determined by recording UV absorption at 280 nm with reference to a calibration standard by a flow photometer Model 662 with Sensor AF44, both products of Wedgewood Technology, Inc. of San Carlos, Calif. The measurement signal was displayed and printed on a commercial flatbed plotter. Hemoglobin was recovered from fresh bovine blood as described in Example 1 and formed into a solution of 2g/L Hb in 0.005 mol/L potassium phosphate buffer at a pH of 6.2.

Experiment A

The Hb solution was fed at a flow rate of about 2 L/min by means of a displacement pump through an absorptive separation device of substantially the design shown in FIG. 1, equipped with a 30-layer spiral wound module with 4 m² of a strongly acid ion exchange membrane. The UV adsorption of the effluent was continuously detected and recorded.

Experiment B

The Hb solution was fed at a flow rate of about 2 L/min by means of a displacement pump through two parallel-connected stacked module-type devices of the design shown in FIG. 2 having 60 layers corresponding to 16 m² of a strongly acid ion exchange membrane. The UV absorption of the effluent was continuously detected and recorded.

Experiment C

The Hb solution was fed at a flow rate of about 2 L/min by means of a displacement pump through a two-stage unit according to FIG. 5 of an embodiment I-type design, the first stage of which was equipped as in Experiment B with 16 m² of membrane, and the second stage of which was equipped as in Experiment A with an additional 4 m² of membrane, so that the total membrane surface area for stages 1 and 2 was 20 m². The UV absorption of the emerging stream was continuously detected and recorded.

Figure 14:
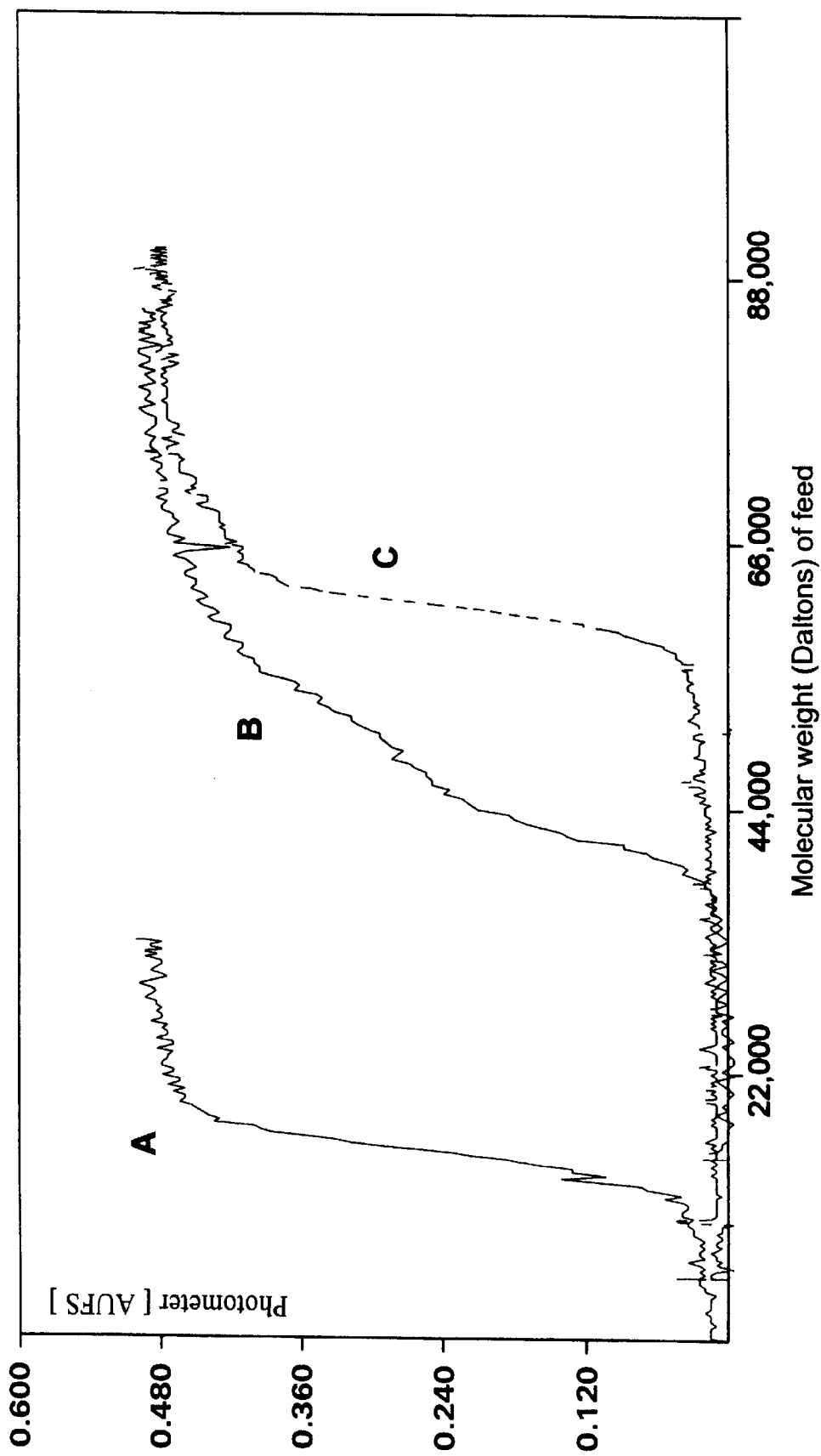
FIG. 14 is a graph showing various hemoglobin breakthrough curves.

The results of experiments A, B and C are graphically shown in FIG. 14. As is apparent from FIG. 14, there was approximately a 50% increase in binding capacity arising from only a 25% increase ($[(20\ m^2-16\ m^2)/20\ m^2]\times 100$) in membrane surface area and up to a 10% increase in breakthrough of the target Hb as well as an improved trend of the breakthrough curve was achieved by the series connection of Experiment C.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A separation device for separations by permeation of liquids through a porous adsorption membrane, comprising:
   (a) a cylindrical housing with liquid input and liquid output;
   (b) said housing accommodating at least one cylindrical adsorber module comprising at least one core mandrel and at least one spiral wound porous adsorption membrane situated around the periphery of said core mandrel, said module arranged substantially concentrically in said housing;
   (c) said module being provided with an annular feed plenum between said core mandrel and said spiral wound membrane and an annular permeate plenum between said spiral wound membrane and said housing; and (d) said feed plenum, said permeate plenum and said liquid input and output being arranged so that liquid feed flows from said liquid input to said feed plenum and permeates through said membrane to said permeate plenum and then is discharged through said liquid output.

2. The separation device of claim 1 wherein said spiral wound porous adsorption membrane comprises more than one wrap of membrane material around said core mandrel.

3. The separation device of claim 1 wherein said liquid input and said liquid output are situated on opposite ends of said housing.

4. The separation device of claim 1, wherein the ratio of height-to-length of said feed and permeate plenums is established by a dimensionless resistance parameter A defined by the equation:

$$A = L \sqrt{\frac{8 \cdot D \cdot d}{[(R_2+k)^2 - R_2^2] \cdot \left[(R_2+k)^2 + R_2^2 - \frac{(R_2+k)^2 - R_2^2}{\ln\left(\frac{R_2+k}{R_2}\right)}\right] \cdot \ln\left(\frac{R_2}{R_1}\right)}}$$

wherein
$R_1$=inside radius of the spiral wound adsorption module in cm;
$R_2$=outside radius of the spiral wound adsorption module in cm;
k=width of the outer annular permeate plenum in cm;
L=length of the spiral wound adsorption module in cm;
D=adsorber membrane flux, measured as $cm^3 \cdot cP/cm^2 \cdot min \cdot bar$; and
d=thickness of the adsorber membrane used in cm.

5. The separation device of claim 4 wherein said parameter A is less than 0.2.

6. The separation device of claim 4 wherein said parameter A is less than 0.1.

7. The separation device of claim 1 wherein said feed and permeate plenums have the same volume.

8. The separation device of claim 7 wherein said feed and permeate plenums have spacers therein.

9. The separation device of claim 8 wherein said spacers are formed by grooves on the surface of said core mandrel and on the inner surface of said housing.

10. The separation device of claim 9 wherein said grooves are helix-shaped.

11. The separation device of claim 10 wherein said adsorber module has an inner support element on its inside surface that is permeable to fluids.

12. The separation device of claim 11 wherein said inner and outer support elements are in a form selected from a perforated tube and fabric mesh.

13. The separation device of claim 1 wherein said adsorber module is enclosed on its outer surface by an outer support element that is permeable to fluids.

14. The separation device of claim 1 wherein said adsorber module comprises adsorption membranes with different adsorption properties.

15. The separation device of claim 14 wherein said adsorber module comprises at least two adsorption membranes having different adsorption properties.

16. The separation device of claim 1 wherein said adsorber module comprises adsorption membranes with different porosities.

17. The separation device of claim 16 wherein those adsorption membranes having relatively greater porosity are arranged on a feed side of said adsorber module.

18. The separation device of claim 14 or 16 or 17 wherein said adsorption membranes are selected from the group consisting of an activated membrane, an affinity membrane, a ligand membrane, an anionic membrane, a cationic membrane, and combinations thereof.

19. The separation device of claim 1, including a replaceable protective filter on a feed side of said adsorber module.

20. The separation device of claim 19 wherein said protective filter comprises a tube-like adsorption membrane.

21. The separation device of claim 20 wherein said protective filter is formed of the same type of adsorption membrane as the adsorption membrane of said adsorber module.

22. The separation device of claim 1 wherein said adsorber module is replaceable.

23. The separation device of claim 22 wherein said connections between said housing and said core mandrel are releasable.

24. The separation device of claim 1 wherein the separation capacity of said device is changeable by varying the number of windings of said adsorption membrane.

25. The separation device of claim 1 wherein said at least one core mandrel comprises multiple cores in fluid communication with each other.

26. The separation device of claim 25 wherein the permeate from one adsorber module comprises the feed to the next succeeding adsorber module.

27. A filtration array comprising a multiplicity of separation devices in fluid communication with each other and wherein each separation device of said multiplicity comprises:

a) a cylindrical housing with liquid input and liquid output;

(b) said housing accommodating at least one cylindrical adsorber module comprising at least one core mandrel and at least one spiral wound porous adsorption membrane situated around the periphery of said core mandrel, said module arranged substantially concentrically in said housing;

(c) said module being provided with an annular feed plenum between said core mandrel and said spiral wound membrane and an annular permeate plenum between said spiral wound membrane and said housing; and (d) said feed plenum, said permeate plenum and said liquid input and output being arranged so that liquid feed flows from said liquid input to said feed plenum and permeates through said membrane to said permeate plenum and then is discharged through said liquid output.

28. The filtration array of claim 27 wherein said separation devices are connected in parallel.

29. The filtration array of claim 27 wherein said separation devices are connected in series.

30. The filtration array of claim 27 wherein said separation devices are connected in parallel and in series.

31. The filtration array of claim 27 wherein said separation devices are connected in tandem.

32. The filtration array of claim 27, including a process controller for automatic operation of said array.

* * * * *

UNITED STATES PATENT AND TRADEMARK OFFICE
CERTIFICATE OF CORRECTION

PATENT NO.    : 6,294,090 B1
DATED         : September 25, 2001
INVENTOR(S)   : Nussbaumer et al.

It is certified that error appears in the above-identified patent and that said Letters Patent is hereby corrected as shown below:

Column 6,
Line 24, delete "p1".

Column 17,
Line 34, delete bold "0" (zero) and insert regular -- O -- (the letter).

Column 22,
Line 49, Italicize "g" after "3000".

Signed and Sealed this

Eighteenth Day of November, 2003

JAMES E. ROGAN
*Director of the United States Patent and Trademark Office*